(12) United States Patent
Grudinin et al.

(10) Patent No.: US 9,188,835 B2
(45) Date of Patent: *Nov. 17, 2015

(54) OPTICAL SOURCES

(71) Applicant: Fianium Ltd., Southampton (GB)

(72) Inventors: Anatoly Grudinin, Southampton (GB); John Clowes, New Milton (GB); Pascal Dupriez, Leognan (FR); Michael Yarrow, Fareham (GB)

(73) Assignee: Fianium Ltd., Southampton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,169

(22) Filed: Jul. 21, 2014

(65) Prior Publication Data

US 2014/0333993 A1    Nov. 13, 2014

Related U.S. Application Data

(63) Continuation of application No. 13/522,594, filed as application No. PCT/GB2011/050106 on Jan. 24, 2011, now Pat. No. 8,785,884.

(30) Foreign Application Priority Data

Jan. 22, 2010 (GB) .................................. 1001051.0

(51) Int. Cl.
*G01N 21/64* (2006.01)
*G02B 21/00* (2006.01)
(Continued)

(52) U.S. Cl.
CPC ............ *G02F 1/395* (2013.01); *G01N 21/6458* (2013.01); *G02B 21/0032* (2013.01);
(Continued)

(58) Field of Classification Search
CPC .......... G01N 21/6458; G01B 21/0032; G01B 21/0076; G02F 1/3536
USPC ........................................... 250/458.1, 459.1
See application file for complete search history.

(56) References Cited

U.S. PATENT DOCUMENTS

| 2004/0135079 | A1 | 7/2004 | Moellmann |
| 2008/0059135 | A1 | 3/2008 | Murugkar et al. |
| 2009/0141340 | A1 | 6/2009 | Sharping et al. |

FOREIGN PATENT DOCUMENTS

WO    WO 2009024529 A1 *  2/2009

OTHER PUBLICATIONS

Courvoisier et al., Using a continuum of light in STED confocal microscopy, Apr. 14, 2006, Proc. SPIE 6191—Conference Volume: Biophotonics and New Therapy Frontiers, vol. 6191, pp. 619108-1 to 619108-10.*

(Continued)

*Primary Examiner* — David Porta
*Assistant Examiner* — Jeremy S Valentiner
(74) *Attorney, Agent, or Firm* — Peter Rainville

(57) ABSTRACT

An optical source 10 comprising an optical output 12, a pump optical source 14, an optical splitter arranged to receive an optical signal from the pump optical source and to split the optical signal into a pump signal and a seed pump signal. A seed signal forming apparatus 18 is arranged to receive the seed pump signal at the pump wavelength and to transform the seed pump signal into a seed signal at a seed wavelength. A first microstructured optical fiber (MSF1) 20 is arranged to receive the pump signal and the seed signal. MSF1 is arranged to cause the pump signal to undergo four-wave mixing seeded by the seed signal on transmission through MSF1 such that a first optical signal at a signal wavelength and second optical signal at an idler wavelength are generated. One of the signal wavelength and the idler wavelength are the seed wavelength and one of the first and second optical signals are provided to the optical output.

20 Claims, 17 Drawing Sheets

(51) Int. Cl.
*G02F 1/39* (2006.01)
*G02F 1/35* (2006.01)
*H01S 3/00* (2006.01)
*H01S 3/067* (2006.01)
*H01S 3/16* (2006.01)

(52) U.S. Cl.
CPC .......... G02B21/0076 (2013.01); G02F 1/3532 (2013.01); G02F 1/3536 (2013.01); *G02F 2001/3507* (2013.01); *G02F 2001/3528* (2013.01); *G02F 2001/392* (2013.01); *G02F 2202/32* (2013.01); *H01S 3/005* (2013.01); *H01S 3/067* (2013.01); *H01S 3/06741* (2013.01); *H01S 3/1618* (2013.01)

(56) References Cited

OTHER PUBLICATIONS

Kudlinkski et al., "Zero-dispersion wavelength decreasing photonic crystal fibers for ultraviolet-extended supercontinuum generation," Optics Express vol. 14, No. 12, pp. 5715-5722 (2006).*
A. Kudlinkski et al., "Zero-dispersion wavelength decreasing photonic crystal fibers for ultraviolet-extended supercontinuum generation," Optics Express vol. 14, No. 12, pp. 5715-5722 (2006).
Reply to EPO from EP11702078.4 (which published as EP2526458) dated Mar. 11, 2013 (8 pages).
Reply to EPO from EP11702078.4 (which published as EP2526458) dated Jun. 16, 2014 (4 pages).
Decision to Grant Patent from EPO in EP 11702078.4 as EPO Patent EP 2526458 dated May 8, 2015 (2 pages).

* cited by examiner

OPTICAL SOURCES

CROSS-REFERENCE TO RELATED APPLICATIONS

The present application is a continuation of application Ser. No. 13/522,594, filed Jul. 17, 2012 and entitled "Optical Sources". Application Ser. No. 13/522,594 claims priority to International PCT Patent Application PCT/GB2011/050106, bearing an International Filing Date of 24 Jan. 2011 and also entitled "Optical Sources." PCT/GB2011/050106 claims priority to Patent Application GB 1001051.0, filed 22 Jan. 2010. The foregoing applications are incorporated herein by reference.

FIELD OF THE INVENTION

The invention can include many aspects, including methods and apparatus relating to optical sources, such as tuneable optical sources, suitable for a variety of applications, including applications as sources in fluorescence imaging apparatus, including flow cytometry apparatus and confocal and stimulated emission depletion (STED) microscopy apparatus. Aspects of the invention can also include methods and apparatus relating to the aforementioned fluorescent imaging apparatus, including flow cytometry apparatus, as well as confocal and STED microscopy apparatus.

BACKGROUND

Many imaging applications, such as fluorescence imaging and stimulated emission depletion (STED) microscopy (first reported by S. Hell et al, "Breaking the diffraction resolution limit by stimulated emission: stimulated emission depletion microscopy", Optics Letters, 19, 1994), can require high power, spatially coherent pulsed light sources operating in the UV, visible and near Infra red regions of the optical spectrum. Many existing pulsed optical sources are either optically very complex, and therefore expensive, or are not able to provide optical pulses of sufficiently high power and frequency at the desired wavelengths.

For example, high power pulsed laser systems, such as a mode-locked Ti:sapphire laser are typically used in STED microscopy to provide a high-intensity depletion pulse. However, these sources suffer the problem that the optimum pulse length for the laser system is much shorter (200-300 fs) than the optimum pulse length for STED (0.1-2 ns), and the pulses must therefore be stretched by a dispersive element, adding complexity to the system. Furthermore, the output wavelength for Ti:Sapphire lasers is typically restricted to between approximately 700 nm and 1 um, meaning that the source cannot be used directly to deplete dyes requiring shorter wavelengths. In order to overcome this, a Ti:Sapphire source can be followed by an optical parametric amplifier (OPA) to generate tuneable visible light. However, the complexity and cost of this approach can in many instances make it suitable only for laboratory research systems.

An alternative STED source has been proposed based on a supercontinuum laser customized to provide high pulse energy spectral density in the red region of the spectrum (Dominik Wildanger et al, "STED microscopy with a supercontinuum laser source", Optics Express, Vol. 16, No. 1, 23 Jun. 2008). Although this approach gives high quality still images, its relatively low operating frequency (of the order of 1 MHz to a few MHz) means that it can typically not readily be adapted for use with high scanning speeds or video-rate imaging. In fluorescence imaging applications such as confocal microscopy and flow cytometry for example, as many as eight different excitation beams can be required, covering the UV and visible regions of the spectrum (350 nm to 700 nm). These are typically provided as multiple discrete laser systems or a supercontinuum laser with a suitable tuneable optical filter, such as a multi-channel acousto-optic filter. Most of the time, only a single wavelength is used at a given time, and therefore the other wavelengths are either in the off-state or their outputs pass into a beam dump or beam deflector when not required. In addition, laser diodes are available at only a select number of wavelengths and these wavelengths do not always coincide with optimum excitation wavelengths of commercially available fluorescent dyes. Providing multiple discrete laser systems results in a very complex and hence expensive instrument and a supercontinuum laser capable of generating an extremely high average power would be required in order to provide excitation beams of sufficient power for imaging applications.

Supercontinuum fibre lasers are commercially available, delivering in excess of 5 mW/nm spectral power density. Supercontinuum lasers based on microstructured or photonic crystal fibres were first proposed by Ranka (U.S. Pat. No. 6,097,870). An optical supercontinuum can also be generated within standard optical fibres tapered over short sections to micrometer scale dimensions, as first reported by Birks et al, "Supercontinuum generation in tapered fibers, Optics letters, Vol. 25, No. 19, 2000".

A supercontinuum laser has a major benefit over laser diodes, offering the ability to select any wavelength in the spectrum and therefore to tune to optimum wavelength for a given dye excitation. However, the additional losses through a tuneable filter (AOTF for example) and launch into optical fibre, mean that the output spectral brightness of this source is significantly lower than a discrete laser diode, restricting use within high-end imaging systems. Moreover, when interested in only a single wavelength at any time, supercontinuum lasers are relatively inefficient sources. With supercontinuum spectra spanning up to 2 micrometers, a 10 nm band of this spectrum constitutes only 0.5 percent of the total optical power, with the remaining 99.5% unused at any time. Coupled with a wall-plug efficiency in the region of a few percent, the total efficiency of a supercontinuum source with AOTF is very low in comparison to laser diodes.

STED microscopy utilising two different colour depletion beams has also been proposed, by Donnert et al, "Two-color far-field fluorescence nanoscopy", Biophysical Journal: Biophysical Letters, L67-L69, 2007.

SUMMARY

According to a first aspect of the invention there is provided an optical source comprising:

an optical output arranged to output an output optical signal;

a pump optical source arranged to generate an optical signal at a pump wavelength;

an optical splitter arranged to receive the optical signal and to split the signal into a pump signal and a seed pump signal;

seed signal forming apparatus arranged to receive the seed pump signal at the pump wavelength and to transform the seed pump signal into a seed signal at a seed wavelength; and a first microstructured optical fibre arranged to receive the pump signal and the seed signal at substantially the same time, the first microstructured optical fibre being arranged to cause the pump signal to undergo four-wave mixing seeded by the seed signal on transmission through the first microstructured optical fibre such that a first optical signal at a signal wavelength and second optical signal at an idler wavelength are generated, one of the signal wavelength and the idler wavelength being the seed wavelength and one of the first and second optical signals being provided to the optical output to form the output optical signal.

An optical source is therefore provided based on seeded four-wave mixing in which the seed signal and the pump signal are provided from a single pump source. The use of seeded four-wave mixing may reduce the noise of the four-wave mixing process, reduce the spectral line width of the resulting first and second optical signals and improve the efficiency of the four wave mixing process.

In an embodiment, the seed signal forming apparatus comprises an optical element arranged to cause the seed pump signal to undergo a non-linear optical process on transmission through the optical element, the non-linear optical process transforming at least a part of the seed pump signal into the seed signal at the seed wavelength.

In an embodiment, the seed signal forming apparatus comprises: a first optical fibre arranged to cause the seed pump signal to undergo spectral broadening on transmission through the first optical fibre to thereby form an optical supercontinuum signal; and a first optical filter having a filter bandwidth and being arranged to receive the optical supercontinuum signal and to select a part of the optical supercontinuum signal within the filter bandwidth.

An optical filter is understood to mean an optical device which transmits only a part of the spectral range of a received optical signal.

In an embodiment, the first optical filter is a wavelength tuneable optical filter. The first optical filter may alternatively have a substantially fixed transmission wavelength.

Forming the seed signal by selecting a part of an optical supercontinuum signal enables the wavelength of the seed signal to be easily tuned in order to select between seeding the first optical signal at the signal wavelength and the second optical signal at the idler signal, and to allow a seed signal wavelength to match that of the first optical signal or the second optical signal, thereby enabling a tuneable pump optical source to be used.

In an embodiment, the seed signal forming apparatus comprises a further microstructured optical fibre arranged to cause the seed pump signal to undergo four-wave mixing on transmission therethrough such that a first signal seed at the signal wavelength and a second signal seed at the idler wavelength are thereby generated; and a second optical filter arranged to select one of the first signal seed and the second signal seed to form the seed signal.

In an embodiment, the further microstructured optical fibre has substantially the same fibre properties as the first microstructured optical fibre.

In an embodiment, the second optical filter comprises a narrow band optical filter having a filter bandwidth and arranged to transmit one of the first signal seed and the second signal seed within the filter bandwidth. The narrow band optical filter may comprise a wavelength tuneable optical filter or may comprise an optical filter having a substantially fixed transmission wavelength.

Forming the seed signal through four-wave mixing within the further microstructured optical fibre ensures that the seed signal wavelength matches that of the signal wavelength or the idler wavelength, as required. This also enables a tuneable pump optical source to be used, with the seed signal wavelength tuning to match the signal or idler wavelength as the pump wavelength is varied.

In an embodiment, the first microstructured optical fibre has a normal dispersion at the pump wavelength.

In an embodiment, the optical source further comprises a second microstructured optical fibre arranged to receive a second pump signal comprising one of the first and second optical signals from the first microstructured optical fibre and to cause the second pump signal to undergo four-wave mixing on transmission through the second microstructured optical fibre such that a third optical signal at a second signal wavelength and a fourth optical signal at a second idler wavelength are generated, one of the third and fourth optical signals being provided to the optical output instead of or in addition to said one of said first and second optical signals Provision of the second microstructured optical fibre enables cascaded four-wave mixing to be performed, and enables the wavelength of the optical signals output from the optical source to be further tuned or generated over a broader spectral range than that achievable with a single four-wave mixing process.

In an embodiment, the first optical filter comprises a wavelength dependent optical splitter arranged to split the optical supercontinuum signal into a first part comprising the seed signal and a second part comprising a transmitted optical supercontinuum signal. In an embodiment, the wavelength dependent optical splitter comprises an acousto-optic filter.

In an embodiment, the seed signal forming apparatus further comprises a third optical filter having a second filter bandwidth and being arranged to receive the transmitted optical supercontinuum signal and to select a part of the transmitted optical supercontinuum signal within the second filter bandwidth to form a second seed signal at a second seed wavelength, the seed signal forming apparatus further being arranged to deliver the second seed signal to the second microstructured optical fibre such that the second pump pulse undergoes four-wave mixing seeded by the second seed signal, such that one of the second signal wavelength and the second idler wavelength comprises the second seed wavelength.

The seed signal forming apparatus can therefore seed the four-wave mixing in both the first and the second microstructured optical fibres, from a single supercontinuum signal.

In an embodiment, the seed signal forming apparatus further comprises an optical splitter arranged to receive the seed signal and to split it into a first part to be provided to the first microstructured optical fibre and a second part to form a second seed pump signal and the optical source further comprises second seed signal forming apparatus arranged to receive the second seed pump signal and to transform the second seed pump signal into a second seed signal at a second seed wavelength, the second seed signal forming apparatus being arranged to deliver the second seed signal to the second microstructured optical fibre such that the second pump signal undergoes four-wave mixing seeded by the second seed signal, such that one of the second signal wavelength and the second idler wavelength comprises the second seed wavelength.

The first and second seed signals can therefore be provided which originate from a single optical signal at the pump wavelength, and which can both be controlled to arrive at the respective microstructured optical fibres at the same time as the respective pump pulses.

In an embodiment, the second seed signal forming apparatus comprises a second further microstructured optical fibre arranged to cause the second seed pump signal to undergo four-wave mixing on transmission therethrough such that a second signal seed at the second signal wavelength and a second idler seed at the second idler wavelength are thereby generated; and a fourth optical filter arranged to select one of the second signal seed and second the idler seed to form the second seed signal.

In an embodiment, the second further microstructured optical fibre has substantially the same fibre properties as the second microstructured optical fibre.

The second seed signal can therefore be generated to match either the second signal wavelength or the second idler wavelength. The second further microstructured optical fibre enables a tuneable pump optical source to be used whilst ensuring that the second seed signal wavelength will tune also, to match the second signal wavelength or the second idler wavelength.

In an embodiment, the second microstructured optical fibre has a normal dispersion at the second pump wavelength.

In an embodiment, the fourth optical filter comprises a narrow band optical filter having a filter bandwidth and arranged to transmit one of the second signal seed and the second idler seed within the filter bandwidth. The narrow band optical filter may comprise a wavelength tuneable optical filter or may comprise an optical filter having a substantially fixed transmission wavelength.

In an embodiment, the optical source further comprises a non-linear optical element arranged to receive one of the third and fourth optical signals and to transform the received signal into an output signal comprising a further wavelength, the output signal at the further wavelength being provided to the optical output instead of or in addition to the said one of the first and second optical signals and instead of or in addition to the said one of the third and fourth optical signal. The non-linear optical element enables the output wavelength of the optical source to be further varied, to cover further wavelength ranges.

In an embodiment, the non-linear optical element comprises a second optical fibre arranged to receive the said one of the third and fourth optical signal and to cause the received signal to undergo spectral broadening on transmission through the second optical fibre to thereby form a further optical supercontinuum signal.

In an embodiment, the non-linear optical element comprises a third further microstructured optical fibre arranged to receive the said one of the third and fourth optical signals and to cause the received signal to undergo four-wave mixing on transmission through the third further microstructured optical fibre such that a fifth optical signal at a further signal wavelength and a sixth optical signal at a further idler wavelength are thereby generated, one of the first and sixth optical signals being provided to the optical output instead of or in addition to the said one of the first and second optical signals and instead of or in addition to the said one of the third and fourth optical signal.

In an embodiment, the non-linear optical element comprises a non-linear crystal or an optical fibre arranged to receive the said one of the third and fourth optical signals and to cause the received signal to undergo second or higher order harmonic generation on transmission through the non-linear optical element.

In an embodiment, the pump optical source comprises a wavelength tuneable laser or a plurality of substantially fixed wavelength lasers each operable at a different one of a said plurality wavelengths. A selectable pump wavelength may therefore be provided. The pump optical source may alternatively comprise a laser having a substantially fixed wavelength. In an embodiment, the pump optical source further comprises an optical amplifier.

In an embodiment, the optical signal comprises an optical pulse and the optical source is arranged such that the first microstructured optical fibre receives the pump pulse and the seed pulse at substantially the same time and the second microstructured optical fibre is arranged to receive the second pump pulse and the second seed pulse at substantially the same time. The seed pulses and the pump pulses may therefore be coherent and timed to arrive together at the respective microstructured optical fibre.

In an embodiment, the pump optical source is arranged to generate a plurality of optical pulses and is further arranged to vary at least one of the pulse duration and frequency of the optical pulses.

A second aspect of the invention provides a wavelength tuneable optical source comprising:

an optical output arranged to output an optical signal;

a wavelength tuneable pump optical source arranged to generate a pump signal at one of a plurality of pump wavelengths;

a first microstructured optical fibre arranged to receive the pump signal, the first microstructured optical fibre being arranged to cause the pump signal to undergo four-wave mixing on transmission through the microstructured optical fibre such that a first optical signal at a first signal wavelength and a second optical signal at an idler wavelength are generated, at least one of the first signal wavelength and the idler wavelength being within the visible region of the optical spectrum, and one of the first and second optical signals being provided to the optical output.

A wavelength tuneable optical source is thus provided which may produce spatially coherent, high brightness laser light in the visible and near-infra-red (NIR) region of the spectrum, enabling tight focussing and integration into high-end instrumentation. The optical source may allow an enhanced wavelength range and wavelength selection to be provided compared with prior art sources. The optical source enables a required wavelength to be provided through by tuning the pump wavelength. The optical source may further enable the available wavelengths to be selected by selecting one or more fibre parameters of the microstructured fibre.

The optical source may be operated at optical efficiencies in the region of 5%, enabling Watt-level output powers to be achieved for a given wavelength in the visible region of the spectrum.

In an embodiment, the first microstructured optical fibre has a normal dispersion at a said pump wavelength.

In an embodiment, the wavelength tuneable visible light optical source further comprises a non-linear optical element arranged to receive one of the first and second optical signals and to transform the received signal into an output signal comprising a further wavelength within the visible region of the optical spectrum, the output signal being provided to the optical output instead of or in addition to the said one of the first and second optical signals.

In an embodiment, the non-linear optical element comprises a non-linear crystal or an optical fibre arranged to cause the received signal to undergo second or higher order harmonic generation on transmission through the non-linear optical element.

In an embodiment, the pump signal comprises an optical pulse. A wavelength tuneable optical pulse source may therefore be provided which may offer reduced complexity and higher nonlinear conversion efficiency than is available with prior art sources. The optical source may be used within time-resolved imaging applications and steady state imaging applications (through high repetition rate, quasi-continuous wave operation).

A third aspect of the invention provides a visible light optical source comprising: an optical output arranged to output an optical signal;

a pump optical source arranged to generate a pump signal at a pump wavelength; a first microstructured optical fibre arranged to receive the pump signal, the first microstructured optical fibre being arranged to cause the pump signal to undergo four-wave mixing on transmission through the microstructured optical fibre such that a first optical signal at a first signal wavelength is generated; and a second microstructured optical fibre arranged to receive the first optical signal, the second microstructured optical fibre being arranged to cause the first optical signal to undergo four-wave mixing on transmission through the second microstructured optical fibre such that a second optical signal at a second signal wavelength and an idler signal at an idler wavelength are generated, one of the second optical signal and the idler signal being provided to the optical output.

A visible light optical source is thus provided which may produce spatially coherent, high brightness laser light in the visible and near-infra-red (NIR) region of the spectrum, enabling tight focussing and integration into high-end instrumentation. The optical source may allow the output optical signal to have a wavelength within an enhanced wavelength range as compared with prior art sources. The output wavelength may further be selected by selecting one or more fibre parameters of the microstructured fibre. The optical source may be operated at optical efficiencies in the region of 5%, enabling Watt-level output powers to be achieved for a given wavelength in the visible region of the spectrum.

In an embodiment, the pump optical source is arranged to generate a pump signal at one of a plurality of pump wavelengths. A wavelength tuneable visible light optical source is thus provided in which the wavelength of the optical signal output may be tuned by tuning the wavelength of the pump signal.

In an embodiment, the first microstructured optical fibre has a normal dispersion at a said pump wavelength. In an embodiment, the second microstructured optical fibre has a normal dispersion at the first signal wavelength.

In an embodiment, the visible light optical source further comprises a non-linear optical element arranged to receive one of the second optical signal and the idler signal to transform the received signal into an output signal comprising a further wavelength the output signal being provided to the optical output instead of or in addition to the said one of the second optical signal and the idler signal.

In an embodiment, the non-linear optical element comprises a non-linear crystal or an optical fibre arranged to receive one of the second optical signal and the idler signal and to cause the received signal to undergo second or higher order harmonic generation on transmission through the non-linear optical element.

In an embodiment, the pump signal comprises an optical pulse. A visible light optical pulse source may therefore be provided which may offer reduced complexity, and higher nonlinear conversion efficiency than is available with prior art sources. The optical source may be used within time-resolved imaging applications and steady state imaging applications (through high repetition rate, quasi-continuous wave operation).

A fourth aspect of the invention provides a stimulated emission depletion microscopy optical source comprising:
an excitation signal output;
a depletion signal output;
a first optical source arranged to generate an optical supercontinuum signal; and a second optical source arranged to generate by a four-wave mixing process a first optical signal at a signal wavelength and a second optical signal at an idler wavelength, the first optical source being arranged to provide at least part of the optical supercontinuum signal to one of the excitation signal output and the depletion signal output and the second optical source being arranged to provide one of the first optical signal and the second optical signal to the other of the excitation signal output and the depletion signal output.

The stimulated emission depletion, STED, microscopy optical source may allow wavelength tunability throughout the visible range of the spectrum to be provided, The STED microscopy optical source may therefore enable the number of dyes and combination of dyes that can be used in STED microscopy to be increased, since the wavelength of the depletion signal is not restricted to the range from approximately 700 nm upwards, as is the case with the prior art Ti:Sapphire laser based source.

In an embodiment, the second optical source is arranged to generate the first and second optical signals by a cascaded four-wave mixing process. The first optical signal may therefore be generated at a shorter signal wavelength.

In an embodiment, the stimulated emission depletion microscopy optical source comprises: a pump optical source arranged to generate an optical signal at a pump wavelength; and an optical splitter arranged to receive the optical signal and to split the optical signal into a first pump signal and a second pump signal, and the first signal source comprises a first optical fibre arranged to receive the first pump signal, the first optical fibre being arranged to cause the first pump signal to undergo spectral broadening on transmission through the first optical fibre to thereby form the optical supercontinuum signal, and the second signal source comprises a first microstructured optical fibre arranged to receive the second pump signal, the first microstructured optical fibre being arranged to cause the second pump signal to undergo four-wave mixing on transmission through the first microstructured optical fibre such that the first and second optical signals are generated.

The STED microscopy optical source may therefore produce an excitation signal and a depletion signal which are coherent with one another. The STED microscopy optical source enables an optical source based on a single pump source to be provided for STED microscopy. The STED microscopy optical source may be structurally less complex and less expensive than conventional STED microscopy optical sources comprising independent excitation and depletion sources, where the depletion source is typically based on a Ti:Sapphire laser.

In an embodiment, the first optical source is arranged to provide at least part of the optical supercontinuum signal to the excitation signal output and the second optical source is arranged to provide one of the first optical signal and the second optical signal to the depletion signal output.

In an embodiment, the optical source comprises a plurality of depletion signal outputs and a said plurality of second optical sources each arranged to provide a respective first or second optical signal to the respective depletion signal output and the optical splitter is arranged to split the optical signal into an excitation pump signal and a said plurality of depletion pump signals.

The STED microscopy optical source can therefore provide a plurality of depletion signals and an excitation signal all from a single pump signal. The excitation signal is able to provide single or multiple excitation wavelengths and the depletion signals may be used to deplete at a plurality of different wavelengths, enabling simultaneous imaging of a sample labelled with different fluorescent dyes.

In an embodiment, the or at least one second optical source further comprises a second microstructured optical fibre arranged to receive one of the first and second optical signals, the second microstructured optical fibre being arranged to cause the received signal to undergo four-wave mixing on transmission through the second microstructured optical fibre such that a third optical signal at a second signal wavelength and a fourth optical signal at a second idler wavelength are generated, one of the third and fourth optical signals being provided to the respective depletion signal output instead of or in addition to the respective said one of the first and second optical signals. The depletion signal source is therefore arranged to perform cascaded four-wave mixing. A depletion signal may therefore be generated at a wavelength outside the range achievable using the single stage four-wave mixing process.

In an embodiment, the or at least one second optical source further comprises a non-linear optical element arranged to receive one of the first and second optical signals or one of the third and fourth optical signals and to transform the received signal into an output signal comprising a further wavelength, the output signal being provided to the respective depletion signal output instead of or in addition to at least one of the respective said one of the first and second optical signals and the respective said one of the third and fourth optical signals.

In an embodiment, the non-linear optical element comprises a non-linear crystal or an optical fibre arranged to receive the said signal and to cause the received signal to undergo second or higher order harmonic generation on transmission through the non-linear optical element.

In an embodiment, the or at least one second optical source further comprises: an optical splitter arranged to receive the depletion pump signal and to split the depletion pump signal into a pump signal and a seed pump signal; and seed signal forming apparatus arranged to receive the seed pump signal at the pump wavelength and to transform the seed pump signal into a seed signal at a seed wavelength, and the first microstructured optical fibre being arranged to receive the pump signal and the seed signal and to cause the pump signal to undergo four-wave mixing seeded by the seed signal on transmission through the first microstructured optical fibre such that said first and second optical signals are generated, one of the signal wavelength and the idler wavelength being the seed wavelength and one of the first and second optical signals being provided to the respective depletion signal output.

In an embodiment, the seed signal forming apparatus comprises an optical element arranged to cause the seed pump signal to undergo a non-linear optical process on transmission through the optical element, the non-linear optical process transforming at least a part of the seed pump signal into the seed signal at the seed wavelength.

In an embodiment, the seed signal forming apparatus comprises: a second optical fibre arranged to cause the seed pump signal to undergo spectral broadening on transmission through the second optical fibre to thereby form an optical supercontinuum signal; and a first optical filter having a filter bandwidth and being arranged to receive the optical supercontinuum signal and to select a part of the optical supercontinuum signal within the filter bandwidth.

An optical filter is understood to mean an optical device which transmits only a part of the spectral range of a received optical signal.

In an embodiment, the first optical filter is a wavelength tuneable optical filter. The first optical filter may alternatively have a substantially fixed transmission wavelength.

In an embodiment, the seed signal forming apparatus comprises a further microstructured optical fibre arranged to cause the seed pump signal to undergo four-wave mixing on transmission therethrough such that a first seed signal at the signal wavelength and a second seed signal at the idler wavelength are thereby generated; and a second optical filter arranged to select said one of the first seed signal and the second seed signal to form the seed signal. In an embodiment, the second optical filter comprises a narrow band optical filter having a filter bandwidth and arranged to transmit one of the first and second seed signals within the filter bandwidth. The narrow band optical filter may comprise a wavelength tuneable optical filter or may comprise an optical filter having a substantially fixed transmission wavelength.

In an embodiment, the further microstructured optical fibre has substantially the same fibre properties as the first microstructured optical fibre.

In an embodiment, the first microstructured optical fibre has a normal dispersion at the pump wavelength.

In an embodiment, the pump optical source comprises a wavelength tuneable laser. The pump optical source may alternatively comprise a laser having a substantially fixed wavelength.

In an embodiment, the optical signal comprises an optical pulse and the pump signal comprises a pump pulse and the seed signal comprises a seed pulse. In an embodiment, the pump optical source comprises a modelocked laser. At least one of the pulse energy, power and repetition rate may be varied to optimise the performance of a STED microscope in which the STED microscopy optical source is to be used.

In an embodiment, the optical source is arranged such that the first microstructured optical fibre receives the pump pulse and the seed pulse at substantially the same time. The STED microscopy optical source is able to produce an excitation signal pulse and a depletion signal pulse which are synchronized to a single optical source and are coherent with one another.

In an embodiment, the pump optical source comprises a fibre laser. The STED microscopy optical source may therefore be totally integrated within optical fibre, enabling a monolithic solution with no bulk-optic alignment.

In an embodiment, the pump optical source is arranged to vary at least one of the pulse duration and frequency of the pump optical pulse. The pulse duration and frequency of the resulting excitation pulse and depletion pulse may therefore be varied. The STED microscopy optical source therefore enables STED pulses of the optimum pulse duration to be produced, with high optical power. High speed, simultaneous super resolution imaging of a sample labelled with different fluorescent dyes can thus be carried out.

A fifth aspect of the invention provides a stimulated emission depletion microscope comprising a stimulated emission depletion microscopy optical source as described above.

A sixth aspect of the invention provides fluorescence imaging apparatus comprising a wavelength tuneable visible light optical source as described above or a visible light optical source as described above.

In an embodiment, the fluorescence imaging apparatus comprises one of a confocal microscope and a flow cytometer.

In an embodiment, the fluorescence imaging apparatus comprises a wavelength tuneable visible light optical source as described above.

In an embodiment, the fluorescence imaging apparatus comprises a visible light optical source as described above, the pump optical source being arranged to generate a pump signal at one of a plurality of pump wavelengths.

In an embodiment, the fluorescence imaging apparatus comprises a plurality of visible light optical sources as described above, each said visible light optical source being arranged to generate an optical signal at a different wavelength.

A seventh aspect of the invention provides a method of performing stimulated emission depletion microscopy, the method comprising:

providing a sample for analysis, the sample comprising a fluorophore; illuminating a region of the sample with an excitation signal having a first wavelength arranged to cause excitation of the fluorophore; and illuminating a portion of the said region with a depletion signal having a second wavelength arranged to cause stimulated emission of the said excited fluorophore, wherein one of the depletion signal and the excitation signal comprises at least part of an optical supercontinuum signal and the other of the depletion signal and the excitation signal comprises one of a first optical signal at a signal wavelength and a second optical signal at an idler wavelength, the first and second optical signals being generated by a four-wave mixing process In an embodiment, the excitation signal comprises at least part of an optical supercontinuum signal and the depletion signal comprises one of a first optical signal at a signal wavelength and a second optical signal at an idler wavelength, the first and second optical signals being generated by a four-wave mixing process.

In an embodiment, the method comprises generating the excitation signal by optically pumping an optical fibre.

In an embodiment, the method comprises: generating the depletion signal by optically pumping a microstructured optical fibre to produce by the four-wave mixing process a first optical signal at a signal wavelength and a second optical signal at an idler wavelength; and selecting one of said first and second optical signals to comprise the depletion signal.

In an embodiment, the sample further comprises a second fluorophore different to the first fluorophore and the method further comprises:

illuminating a second region of the sample with an excitation signal having a third wavelength arranged to cause excitation of the second fluorophore; and illuminating a portion of the second region with a second depletion beam having a fourth wavelength arranged to cause stimulated emission of the said excited second fluorophore.

In an embodiment, the method comprises: generating the second depletion beam by optically pumping a second microstructured optical fibre to produce by a four-wave mixing process a third optical signal at a second signal wavelength and a fourth optical signal at a second idler wavelength; and selecting one of said third and fourth optical signals to comprise the depletion signal.

The invention also provides a wavelength tunable optical source comprising an optical output arranged to output an optical signal, a wavelength tunable pump optical source arranged to generate a pump optical signal and a microstructured optical fibre arranged to receive the pump optical signal, the microstructured optical fibre being arranged to cause the pump signal to undergo single pass four-wave mixing on transmission through the microstructured optical fibre such that a first optical signal at a signal wavelength and a second optical signal at an idler wavelength are generated, at least one of the first and second optical signals being provided to the optical output and being tunable in wavelength responsive to the tuning of the wavelength of the pump optical source.

The pump optical source is preferably arranged to generate a pump optical signal at a wavelength within the Yb gain bandwidth. The wavelength tunable pump optical source may be tunable between 1055 nm and 1080 nm. Alternatively, the wavelength tunable pump optical source may be tunable between 1035 and 1100 nm. Alternatively, the wavelength tunable pump optical source may be tunable between 1020 nm and 1100 nm.

The microstructured optical fibre may be arranged so that the signal wavelength can be tuned below 1 micron. Preferably, the signal wavelength can be tuned below 900 nm. The signal wavelength may be tunable from approximately 890 nm to 710 nm. Alternatively, the signal wavelength may be tunable between 715 nm and 820 nm. Alternatively, the signal wavelength may be tunable between 720 nm to 809 nm. Alternatively, the signal wavelength may be tunable between 600 nm to 900 nm.

The microstructured optical fibre may be arranged so that the idler wavelength is in the range 1100 nm to 2250 nm.

The pump optical signal may have an average power of about 3 Watts. Alternatively, the pump optical signal may have an average power in the range 8-10 Watts. The pump optical signal may have an average power of greater than 20 Watts.

The first and/or second optical signal may have an average power of about 1 Watt, or alternatively greater than 1 Watt. The first and/or second optical signal may have an average power of about 5 Watts, or alternatively greater than 5 Watts.

The invention also provides a tunable frequency conversion arrangement, comprising: a first nonlinear frequency converter configured for receiving a first optical signal and for generating a second optical signal and a third optical signal; a second nonlinear frequency converter configured to receive at least two of the first, second and third optical signals, wherein the second nonlinear frequency converter is tunable to select one of a plurality of frequency conversion modes, wherein in each of said frequency conversion modes one or more of said at least two received signals are caused to undergo at least one nonlinear process in the second nonlinear frequency converter such that a fourth optical signal is generated.

The second nonlinear frequency converter may comprise a tunable nonlinear element.

The invention also provides a tunable frequency conversion arrangement, comprising: an optical source arranged to generate a first optical signal at a pump wavelength; a microstructured fibre arranged to receive the first optical signal, the microstructured fibre being arranged to cause the first optical signal to undergo four wave mixing on transmission through the microstructured fibre such that a second optical signal at a signal wavelength and a third optical signal at an idler wavelength are generated, and a tunable nonlinear optical element arranged to receive at least two of the first, second and third optical signals, wherein the nonlinear optical element can be tuned to select one of a plurality of frequency conversion modes, wherein in each said frequency conversion mode one or more of said received signals are caused to undergo a nonlinear process on transmission through the nonlinear element such that a frequency-converted optical signal is generated. In an embodiment, the microstructured optical fibre has a normal dispersion at said pump wavelength.

The tunable nonlinear optical element may be arranged so that in one of said frequency conversion modes a frequency-converted optical signal is generated at a first wavelength and in another of said frequency conversion modes a frequency-converted optical signal is generated at a second wavelength different to the first wavelength.

The tunable nonlinear optical element may be arranged so that in one of said frequency conversion modes, at least one of said received signals is caused to undergo a first nonlinear process, and in another of said frequency conversion modes at least one of said received signals is caused to undergo a second nonlinear process different to the first nonlinear process.

For each frequency conversion mode the nonlinear process may comprise one of: (a) sum frequency generation; (b) difference frequency generation; and (c) second or higher harmonic generation.

The plurality of frequency conversion modes may include at least one frequency conversion mode in which two of the received signals are caused to undergo either sum frequency or difference frequency generation on transmission through the nonlinear element.

The plurality of frequency conversion modes may include at least one frequency conversion mode in which one of the received signals is caused to undergo second or higher harmonic generation on transmission through the nonlinear element.

The tunable nonlinear optical element may be arranged to receive the first, second and third optical signals.

The optical source may comprise a tunable optical source arranged to generate the first optical signal at one of a plurality of wavelengths. In this way, a very broad tuning range can be obtained by the frequency conversion arrangement.

In one or more of said frequency conversion modes, a frequency-converted signal at one or more visible wavelengths may be generated.

The pump wavelength may be between 1020 nm and 1100 nm.

Said plurality of frequency conversion modes may comprise one or more frequency conversion modes in which one or more of the received signals are caused to undergo two or more nonlinear processes on transmission through the nonlinear element such that a plurality of frequency-converted optical signals at a plurality of output wavelengths are generated.

The invention also provides a frequency conversion arrangement, comprising: an optical source arranged to generate a first optical signal at a first wavelength; a microstructured fibre arranged to receive the first optical signal, the microstructured fibre being arranged to cause the first optical signal to undergo four wave mixing on transmission through the microstructured fibre such that a second optical signal at a signal wavelength and a third optical signal at an idler wavelength are generated, and a nonlinear optical element arranged to receive at least two of the first, second and third optical signals, wherein the nonlinear optical element is arranged so that said received signals are caused to undergo a nonlinear process on transmission through the nonlinear element such that a frequency-converted optical signal is generated.

The invention also provides a tunable frequency conversion arrangement comprising any one of the optical sources described above, and a tunable nonlinear optical element arranged to receive at least two of the output optical signals of the optical source, wherein the nonlinear optical element can be tuned to select one of a plurality of frequency conversion modes, wherein in each said frequency conversion mode one or more of said received signals are caused to undergo a nonlinear process on transmission through the nonlinear element such that a frequency-converted optical signal is generated.

The invention also provides a coherent anti-stokes Raman scattering imaging method for imaging a sample, comprising: generating a first optical signal having a selected frequency, transmitting the first optical signal through a nonlinear element, thereby causing the first optical signal to undergo a nonlinear process such as four wave mixing such that a second optical signal and a third optical signal are generated; delivering a signal pair comprising two of said first, second and third optical signals to the sample, wherein the frequency of the first optical signal is selected to provide a selected difference frequency between the optical signals of said pair for imaging the sample.

The invention also provides a coherent anti-stokes Raman scattering apparatus for imaging a sample, comprising: an optical output; an optical source arranged to generate a first optical signal at a first wavelength; a nonlinear element arranged to receive the first optical signal, the nonlinear element being arranged to cause the first optical signal to undergo a nonlinear process such as four-wave mixing on transmission through the nonlinear element such that a second optical signal at a second wavelength and a third optical signal at a third wavelength are generated, wherein an optical signal pair comprising two of the first, second and third optical signals is provided to the optical output for imaging the sample.

BRIEF DESCRIPTION OF THE DRAWINGS

Embodiments of the invention will now be described in detail, by way of example only, with reference to the accompanying drawings, in which.

DETAILED DESCRIPTION

Figure 1:
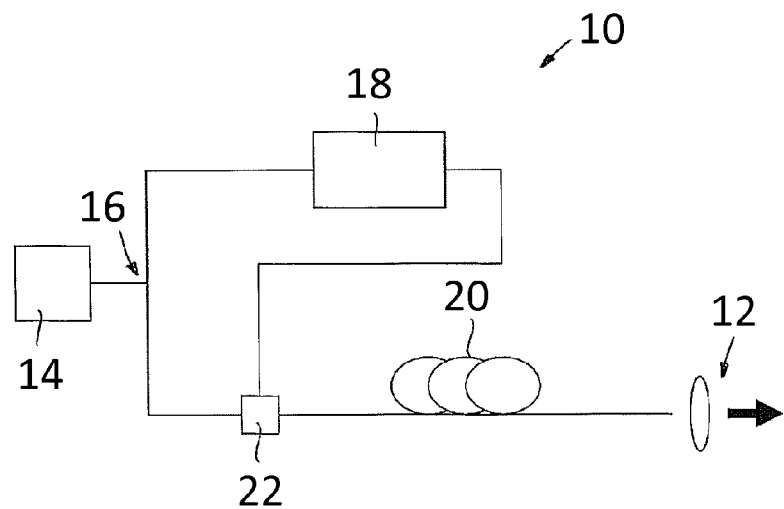
FIG. 1 is a schematic representation of an optical source according to a first embodiment of the invention.

Referring to FIG. 1, a first embodiment of the invention provides an optical source 10 comprising an optical output 12 arranged to output an output optical signal, a pump optical source 14, an optical splitter 16, seed signal forming apparatus 18 and a first microstructured optical fibre (MSF) 20.

The pump optical source 14 is arranged to generate an optical signal at a pump wavelength. The optical splitter 16 is arranged to receive the optical signal and to split the optical signal into a pump signal and a seed pump signal. The optical signal can comprise a pulsed or continuous wave (CW) optical signal, such that the optical source 10 can comprise a pulsed or CW optical source.

The seed signal forming apparatus 18 is arranged to receive the seed pump signal at the pump wavelength. The seed signal forming apparatus 18 is further arranged to transform the seed pump signal into a seed signal at a seed wavelength. The seed signal forming apparatus 18 comprises an optical element arranged to cause the seed pump signal to undergo a non-linear optical process on transmission through the optical element. The non-linear optical process transforms at least a part of the seed pump signal into the seed signal at the seed wavelength.

The seed signal is delivered from the output of the seed signal forming apparatus 18 to the MSF 20 via a wavelength division multiplexer 22. The MSF 20 is arranged to cause the pump signal to undergo four-wave mixing seeded by the seed signal on transmission of the two signals through the MSF 20. A first optical signal at a signal wavelength and a second optical signal at an idler wavelength are thereby generated. The seed wavelength comprises one of the signal wavelength and the idler wavelength. One of the first and second optical signal are provided to the optical output 12, to form the output optical signal.

Four-wave mixing is a third-order nonlinear effect (like self-phase modulation and cross-phase modulation). When two optical signals, having frequencies $\omega_1$ and $\omega_2$ interact in a nonlinear medium two new optical signals, having frequencies $\omega_3$ and $\omega_4$ are generated. Energy conservation requires that $\omega_1+\omega_2=\omega_3+\omega_4$. In order for four-wave mixing to occur effectively phase matching is also required. When a highly intense pump signal with a frequency $\omega_{pump}$ propagates in an optical fibre it induces a refractive index modulation in the glass (Kerr nonlinearity) which also occurs at two phase-matched frequencies $\omega_{idler}$ and $\omega_{signal}$. This in turn creates two new beams with frequencies defined by the energy conservation condition: $\omega_{idler}+\omega_{signal}-2\omega_{pump}=0$ or $2\omega_{pump}=\omega_{idler}+\omega_{signal}$. Phase matching requires that $2k_{pump}=k_{idler}+k_{signal}+2\gamma P$, where k is wavenumber, P is the power of the pump signal and $\gamma$ is the nonlinear parameter (given by:

$$\gamma = \frac{2\pi n_2}{\lambda_p A_{eff}},$$

where $n_2$ is the nonlinear refractive index, $\lambda_p$ is the pump wavelength and $A_{eff}$ is the effective area of the guided mode.) Two pump photons are thus converted into one photon at a signal wavelength (short wavelength) and one photon at an idler wavelength (long wavelength). Four-wave mixing in microstructured optical fibres has been demonstrated by Wadsworth et al, "Supercontinuum generation and four-wave mixing with Q-switched pulses in endlessly single-mode photonic crystal fibres", Optics express, Vol. 12, No. 2, pp. 299-309, 2004.

It will be well known to the person skilled in the art that the energy conservation condition depends on the effective indices of each component and phase matching can be obtained in single mode fibre by choosing adequate dispersion characteristics. The dispersion of microstructured fibres can be controlled by controlling the hole size, hole to hole separation (pitch) and mode field diameter of the fibre. The dispersion of a microstructured fibre can be calculated using the empirical method outlined by Saitoh et al "Empirical relations for simple design of photonic crystal fibres", Optics express Vol. 13, No. 1, pp. 267-275, 2005. Based on this calculation and satisfaction of the phase matching condition, the signal and idler frequencies generated by a given microstructured fibre, when pumped at a defined pump wavelength, can be calculated. It will be appreciated that there are a range of fibre designs capable to delivering a required signal or idler wavelength.

Figure 2:
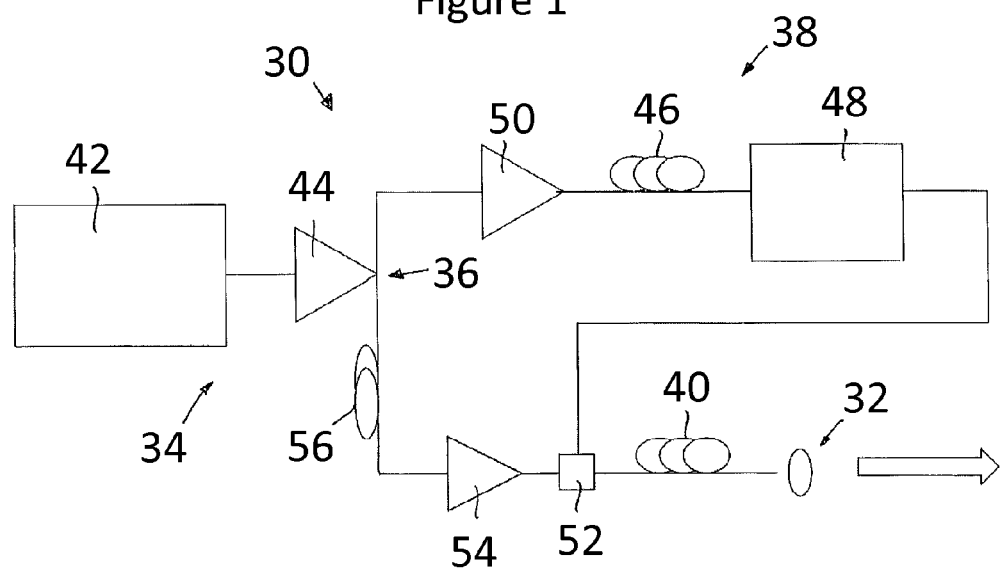
FIG. 2 is a schematic representation of an optical source according to a second embodiment of the invention.

An optical source 30 according to a second embodiment of the invention is shown in FIG. 2. The optical source 30 comprises an optical output 32 arranged to output an output optical signal, a pump optical source 34, an optical splitter 36, seed signal forming apparatus 38 and a first microstructured optical fibre (MSF1) 40.

The pump optical source 34 comprises a pulsed laser 42 arranged to generate an optical signal comprising optical pulses. The optical pulses have a pump wavelength of, in this example 1064 nm, a 20 MHz pulse frequency and a pulse duration of approximately 80 ps. The pump optical source 34 further comprises an optical amplifier 44 arranged to receive the optical pulses from the laser 42 and to amplify the pulses to have an average power in the region of 100 mW The seed signal forming apparatus 38 comprises a first optical fibre 46 and an optical filter 48. A second optical amplifier 50 is provided between the optical splitter 36 and the seed signal forming apparatus 38, and is arranged to amplify the seed pulse prior to receipt by the seed signal forming apparatus 38. The optical fibre 46 is arranged to receive the seed pump pulse and to cause the seed pump pulse to undergo spectral broadening on transmission through the fibre, to form an optical supercontinuum pulse. In this example, the optical fibre 46 comprises an endlessly single mode nonlinear microstructured optical fibre, such as SC-5.0-1040 from NKT Photonics (Denmark) with a zero dispersion wavelength at approximately 1040 nm, having anomalous dispersion at the pump wavelength close to 1064 nm. The resulting optical supercontinuum pulse has a spectral range extending from approximately 500 nm to above 1.75 μm. The optical fibre 46 may alternatively comprise a tapered optical fibre or a tapered microstructured optical fibre such that an optical supercontinuum pulse is generated due to a resulting nonlinear interaction of the pump signal with the fibre.

The optical filter 48 in this example has a filter bandwidth of approximately 1 nm and a transmission wavelength of 742 nm optimised to the system. This filter can be selected according to the system design and application requirements. The optical filter 48 is arranged to receive the optical supercontinuum pulse and to select a part of the pulse within the filter bandwidth, to form a seed pulse. The seed pulse is delivered to MSF1 40 via a wavelength division multiplexer 52. MSF1 40 has a length of 1.5 meters, a hole diameter of 0.9 micrometers, a hole pitch of 3 micrometers, mode field diameter of approximately 5 micrometers and a zero dispersion wavelength of approximately 1103 nm. A third optical amplifier 54 is provided between the splitter and MSF1 40 and is arranged to amplify the pump pulses to an energy of approximately 500 nJ and a corresponding peak power in the region of 6 kW. MSF1 40 is arranged to receive the seed pulse and the pump pulse at substantially the same time. An optical delay line 56 is provided in the path of the pump pulse, between the optical splitter 36 and the third optical amplifier 54, in order to control the time of flight of the pump pulse to MSF1 such that the seed pulse and the pump pulse overlap temporally. MSF1 40 is arranged to cause the pump pulse to undergo four-wave mixing seeded by the seed pulse on transmission of the two pulses through the fibre. A first optical signal pulse at a signal wavelength of 742 nm and second optical signal pulse at an idler wavelength of approximately 1860 nm are generated.

It will be appreciated that the actual signal wavelength and idler wavelength may be changed by varying one or more of the fibre parameters of MSF1, including the zero dispersion wavelength, hole size and hole pitch. In this example, the pulse laser 42 has a fixed wavelength but the optical pulse source 30 may be modified to use a tuneable wavelength laser, to provide for tuning of the signal wavelength and the idler wavelength. In this arrangement, the optical filter 48 is wavelength tuneable such that the filter wavelength may be tuned to match a desired signal wavelength or idler wavelength of MSF1.

In this example, the seed wavelength is selected to be the signal wavelength, so that the seed pulse seeds the first optical signal and the first optical signal is provided to the optical output 32. It will be appreciated that the seed wavelength may alternatively be selected to be the idler wavelength, which in this example falls within the near infra-red (NIR) region of the spectrum, such that the second optical signal is seeded. The output of the optical source 30 can therefore be selected to be in the visible region or in the NIR region of the spectrum by selecting the seed wavelength and the appropriate one of the first and second optical signals. It will also be appreciated that the pulse duration of the pulse laser 42 can be changed to suit a particular application of the optical source 30, and can be substantially shorter than 80 ps or substantially longer than 80 ps. The optimum pulse duration will depend on the particular application, a desired four-wave mixing efficiency and any nonlinear spectral broadening (due to Kerr nonlinearity) introduced by amplifiers and fibre between the pulsed laser 42 and MSF1.

It will be appreciated that the optical pulse source 42 may alternatively comprise a continuous wave (CW) optical source.

Figure 3:
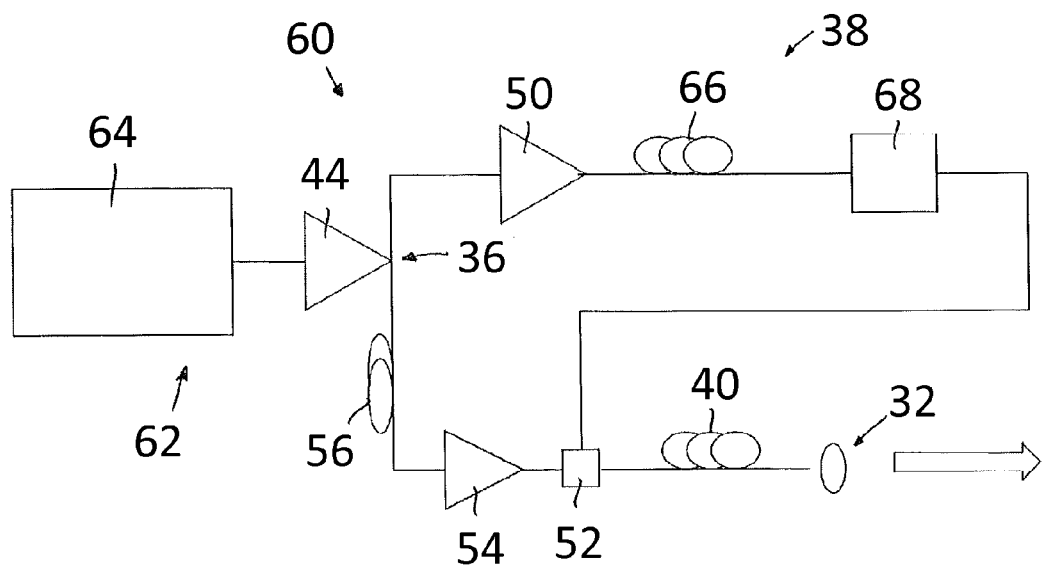
FIG. 3 is a schematic representation of an optical source according to a third embodiment of the invention.

A third embodiment of the invention provides an optical source 60, as shown in FIG. 3. The optical source 60 is substantially the same as the optical source 30 of the previous embodiment, with the following modifications. The same reference numbers are retained for corresponding features.

In this example, the pump optical source 62 comprises a wavelength tuneable pulse laser 64 operable to generate optical pulses at a pump wavelength tuneable between 1055 nm and 1080 nm. The optical pulses have a pulse frequency of 20 MHz, a pulse duration of 80 ps. The optical amplifier 44 is arranged to receive the pulses from the laser 64 and to amplify them to an average optical power of approximately 100 mW.

In this embodiment, the seed signal forming apparatus comprises a second microstructured optical fibre (MSF2) 66 of the same type and length as MSF1 40. MSF2 is arranged to receive the seed pump pulse and to cause the seed pump pulse to undergo four-wave mixing on transmission through the fibre 66, a signal seed and an idler seed are thereby generated. Since MSF2 66 is the same as MSF1 40, the signal seed is at the signal wavelength and the idler seed is at the idler wavelength. The seed signal forming apparatus further comprises an optical filter 68 arranged to select one of the signal seed and the idler seed to form the seed signal for delivery to MSF1 40.

When the wavelength of the laser 64 is tuned, the wavelength of the first and second optical signals output from MSF1 40 will correspondingly change, the wavelength of the signal seed and the idler seed output from MSF2 66 will correspondingly change, such that their wavelengths remain matched to those of the signal wavelength and the idler wavelength. Automatic, matched tuning of the seed pulse wavelength is therefore provided. Four-wave mixing signal wavelengths in the range of approximately 715 nm to 820 nm and corresponding idler wavelength in the range of 2050 nm to 1575 nm are generated by the MSF when pumped by the pump laser operating in the range from 1055 nm to 1080 nm respectively.

Figure 4:
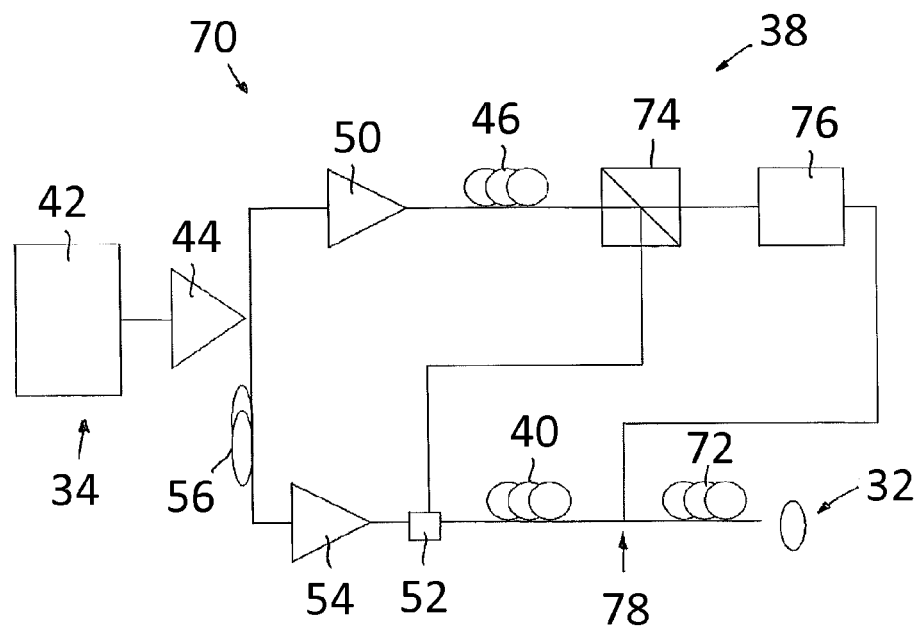
FIG. 4 is a schematic representation of an optical source according to a fourth embodiment of the invention.

Referring to FIG. 4, a fourth embodiment of the invention provides an optical source 70. The optical source 70 is substantially the same as the optical source 30 of FIG. 2, with the following modifications. The same reference numbers are retained for corresponding features.

In this embodiment, the pulsed laser source 42 operates at a fixed wavelength of approximately 1064 nm and MSF1 40 produces a first optical signal at a signal wavelength of approximately 742 nm and a second optical signal at an idler wavelength of approximately 1860 nm. The optical source 70 further comprises a third microstructured optical fibre (MSF3) 72. The third microstructured optical fibre (MSF3) 72 has a length of 1.0 meters, a hole diameter of 1.7 micrometers, a hole pitch of 2 micrometers, mode field diameter of approximately 2.2 micrometers and a zero dispersion wavelength of approximately 811 nm. MSF3 72 is arranged to receive a second pump signal, which comprises one of the first and second optical signals output from MSF1 40.

It will be appreciated that through cascaded four-wave mixing there are many more combinations of microstructured fibre parameters capable of producing a signal or idler wavelength in the visible or near-infra red (NIR) region of the spectrum.

In this example, the seed signal forming apparatus 38 comprises a first optical filter 74 in the form of an acousto-optic tuneable filter (AOTF). The AOTF 74 is arranged to receive the optical supercontinuum pulse from the optical fibre 46 and to select a part of the optical supercontinuum pulse to form a first seed pulse for MSF1 40 and to transmit the remaining part of the supercontinuum pulse to form a second seed pump pulse. The AOTF 74 diffracts the wavelength for the first seed pulse into the first order and the remaining wavelengths, forming the transmitted part of the optical supercontinuum pulse, are diffracted into the zero order.

In this embodiment, the seed signal forming apparatus 38 further comprises a second acousto-optic tuneable filter (AOTF) 76 having a filter bandwidth of approximately 1 nm, tuneable over a wavelength range from 400 nm to 650 nm. The second AOTF 76 is arranged to select a part of the transmitted optical supercontinuum pulse within its filter bandwidth to form a second seed pulse. The second seed pulse is delivered to MSF3, via an optical coupler 78.

MSF3 72 is arranged to receive the second pump pulse and the second seed pulse at substantially the same time, and a further delay line may be provided between MSF1 40 and MSF3 72 in order to control the time of arrival of the second pump pulse. MSF3 72 is arranged to cause the second pump pulse to undergo four-wave mixing seeded by the second seed pulse as the second pump pulse and the second seed pulse are transmitted through the fibre. A third optical signal pulse at a second signal wavelength of 450 nm and a fourth optical signal pulse at an idler wavelength of approximately 2250 nm are generated. One of the third and fourth optical signals are provided to the optical output 32 instead of one of the first and second optical signals. It will be appreciated however that one of the third and fourth optical signals and one of the first and second optical signals may alternatively provided to the optical output 32, forming an output optical signal comprising both wavelengths.

Figure 5:
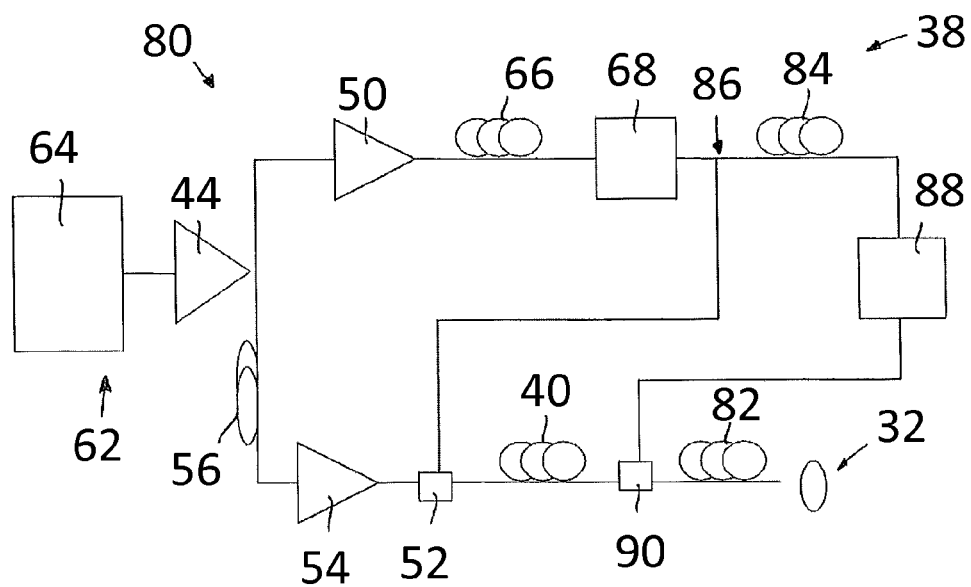
FIG. 5 is a schematic representation of an optical source according to a fifth embodiment of the invention.

A fifth embodiment of the invention provides an optical source 80, as shown in FIG. 5. The optical source 80 is substantially the same as the optical source 60 of FIG. 3, with the following modifications. The same reference numbers are retained for corresponding features.

In this embodiment, the optical source 80 further comprises a third microstructured optical fibre (MSF3) 82. MSF3 82 is arranged to receive a second pump signal, which comprises one of the first and second optical signals output from MSF1 40. The seed signal forming apparatus further comprises a fourth microstructured optical fibre (MSF4) 84 of the same type and length as MSF3 82. The seed signal forming apparatus 38 further comprises an optical splitter 86 arranged to receive the seed signal from the optical filter 68 and to split the seed signal into a first part to form a first seed signal for MSF1 40 and a second part to form a second seed pump signal for MSF4 84. MSF4 84 is arranged to receive a second seed pump signal and to cause the second seed pump signal to undergo four-wave mixing on transmission through the fibre 84, to thereby generate a second signal seed and a second idler seed. The seed signal forming apparatus 38 further comprises a second optical filter 88 arranged to select one of the second signal seed and the second idler seed to form a second seed signal for delivery to MSF3 82. The second seed signal is coupled to MSF3 82 via a second wavelength division multiplexer 90.

MSF3 82 is arranged to receive the second pump signal and the second seed signal and is arranged to cause the second pump signal to undergo four-wave mixing seeded by the second seed signal. A third optical signal at a second signal wavelength and a fourth optical signal at a second idler wavelength are thereby generated. One of the third and fourth optical signals are provided to the optical output 32.

In this example, the pump optical source comprises a wavelength tuneable pulse laser 64. The second pump signal therefore comprises a second pump pulse and the second seed signal comprises a second seed pulse, the timings of the pulses are arranged so that they arrive at MSF3 82 at substantially the same time and temporally overlap during transmission through the fibre.

When the wavelength of the laser 64 is tuned, the wavelength of the first and second optical signals output from MSF1 40 will correspondingly change and the wavelengths of the third and fourth optical signals output from MSF3 82 will correspondingly change. The wavelengths of the signal seed and the idler seed output from MSF2 66 will correspondingly change, such that their wavelengths remain matched to those of the signal wavelength and the idler wavelength, and the wavelengths of the second signal seed and the second idler seed output from MSF4 84 will correspondingly change, such that their wavelengths similarly remain matched to those of the second signal wavelength and the second idler wavelength. Automatic, matched tuning of both seed pulse wavelengths is therefore provided.

It will be appreciated that the range of wavelength tunability of the signal and idler outputs from MSF1 and MSF2 and from MSF3 and MSF4 will be dependent on their fibre parameters which can be specifically chosen for a particular application of the optical source. The fibre parameters described in this embodiment result in a tuneable signal output from MSF4 in the range of 450 nm (corresponding to a pulse laser 64 wavelength of 1064 nm) to approximately 610 nm (corresponding to a pulse laser 64 wavelength of 1076 nm). This system therefore provides a tuneable self-seeded four-wave mixing source with output wavelength in the visible region of the spectrum tuneable from below 450 nm in the blue to beyond 610 nm in the red.

Figure 6:
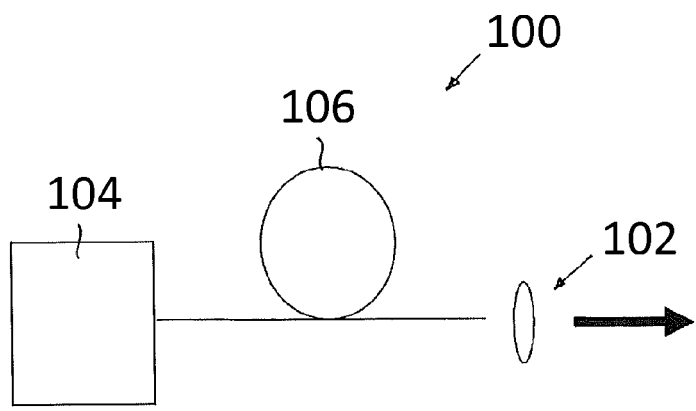
FIG. 6 is a schematic representation of wavelength tuneable optical sources according to a sixth embodiment of the invention.

A sixth embodiment of the invention provides a wavelength tuneable optical source 100, as shown in FIG. 6. The optical source 100 comprises an optical output 102, a pump optical source 104 and a microstructured optical fibre (MSF) 106.

In this example, the pump optical source 104 comprises a wavelength tuneable laser arranged to generate an optical signal at a wavelength in the range 1055 nm to 1080 nm (falling within the gain bandwidth of Ytterbium doped optical fibre lasers and amplifiers). The MSF 106 has a length of 1.5 meters, a hole diameter of 0.9 micrometers, a hole pitch of 3 micrometers, mode field diameter of approximately 5 micrometers and a zero dispersion wavelength of approximately 1103 nm. The MSF 106 is arranged to receive the pump signal and to cause the pump signal to undergo four-wave mixing on transmission through the fibre 106. In this example, a first optical signal having a signal wavelength tuneable across the range of 720 nm to 809 nm is generated. An idler signal having a wavelength tuneable across the range 2250 nm to 1100 nm is also generated. The first optical signal is provided to the optical output 102.

The wavelength of the first optical signal may be tuned by tuning the pump wavelength. The pump optical source may be arranged to generate a pump signal comprising a continuous wave signal or one or more pump pulses.

Figure 7:
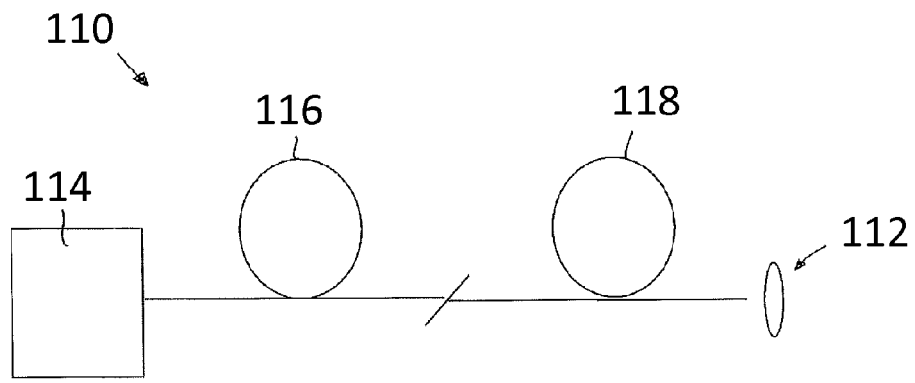
FIG. 7 is a schematic representation of visible light optical source according to a seventh embodiment of the invention.

FIG. 7 shows a visible light optical source 110 according to a seventh embodiment of the invention. The optical source 110 comprises an optical output 112, a pump optical source 114, a first microstructured optical fibre (MSF1) 116 and a second microstructured optical fibre (MSF2) 118.

In this example, the pump optical source 114 comprises a laser arranged to generate an optical signal at a wavelength in the range 1055 nm to 1080 nm (falling within the gain bandwidth of Ytterbium doped optical fibre lasers and amplifiers). MSF1 116 has a length of 1.5 meters, a hole diameter of 0.9 micrometers, a hole pitch of 3 micrometers, mode field diameter of approximately 5 micrometers and a zero dispersion wavelength of approximately 1103 nm. MSF1 116 is arranged to receive the pump signal and to cause the pump signal to undergo four-wave mixing on transmission through the fibre 116. In this example, a first optical signal having a signal wavelength in the range 720 nm to 809 nm is generated. An idler signal having a wavelength in the range 2250 nm to 1100 nm is also generated.

MSF2 118 is arranged to receive the first optical signal from MSF1 116. MSF2 118 is arranged to cause the first optical signal to undergo four-wave mixing on transmission through the fibre 118 such that a second optical signal at a second signal wavelength and an idler signal at an idler wavelength are generated. One of the second optical signal and the idler signal are provided to the optical output 112. In this example, MSF2 118 has a length of 1.0 meters, a hole diameter of 1.7 micrometers, a hole pitch of 2 micrometers, mode field diameter of approximately 2.2 micrometers and a zero dispersion wavelength of approximately 811 nm.

Within a pump wavelength from 1064 nm to 1076 nm the optical source 110 generates a second optical signal through cascaded four-wave mixing at a second signal wavelength of approximately 450 nm and an idler signal having an idler wavelength of approximately 2250 nm An eighth embodiment of the invention provides a visible light optical source which is substantially the same as the visible light optical source 110 shown in FIG. 7.

The same reference numbers are retained for corresponding features and reference is made to FIG. 7.

In this embodiment, the pump optical source 104 comprises a wavelength tuneable pulsed laser arranged to generate optical pulses tuneable in wavelength over the range 1030 nm to 1080 nm. Tuning the pump wavelength over the range 1064 nm to 1076 nm results in a second optical signal being generated at a signal wavelength tuneable from 450 nm to 610 nm and an idler signal at a corresponding idler wavelength of between approximately 2300 nm and 1100 nm.

Figure 8:
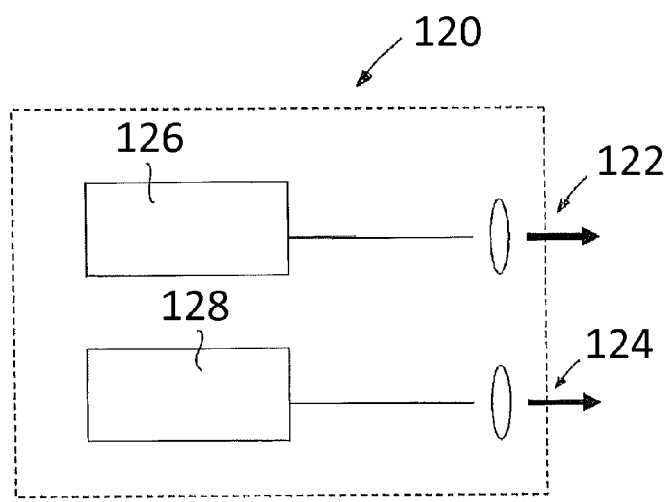
FIG. 8 is a schematic representation of a stimulated emission depletion microscopy optical source according to a ninth embodiment of the invention.

A ninth embodiment of the invention provides a stimulated emission depletion (STED) microscopy optical source 120, as shown in FIG. 8. The STED microscopy optical source 120 comprises an excitation signal output 122, a depletion signal output 124, a first optical source 126 and a second optical source 128.

The first optical source 126 is arranged to generate an optical supercontinuum signal. The second optical source 128 is arranged to generate a first optical signal at a signal wavelength and a second optical signal at an idler wavelength, the first and second optical signals being generated by a four-wave mixing process.

The first optical source is arranged to provide at least part of the optical supercontinuum signal to one of the signal outputs 122, 124, which in this example is shown as the excitation signal output 122. The second optical source 128 is arranged to provide one of the first and second optical signals to the other signal output 122, 124, which in this example is shown as the depletion signal output 124. It will be appreciated that the first optical source may alternatively be arranged to provide the optical supercontinuum signal to the depletion signal output 124 and the second optical source 128 may be arranged to provide one of the first and second optical signals to the excitation signal output 122.

The STED microscopy optical source 120 is therefore able to provide an optical supercontinuum excitation signal and a four-wave mixing based depletion signal.

The excitation signal comprises a broadband output which can be filtered to provide the required wavelength needed to excite a given fluorescent dye. The depletion signal is selected to have a wavelength suitable for depleting the fluorescent dye through stimulated emission.

Figure 9:
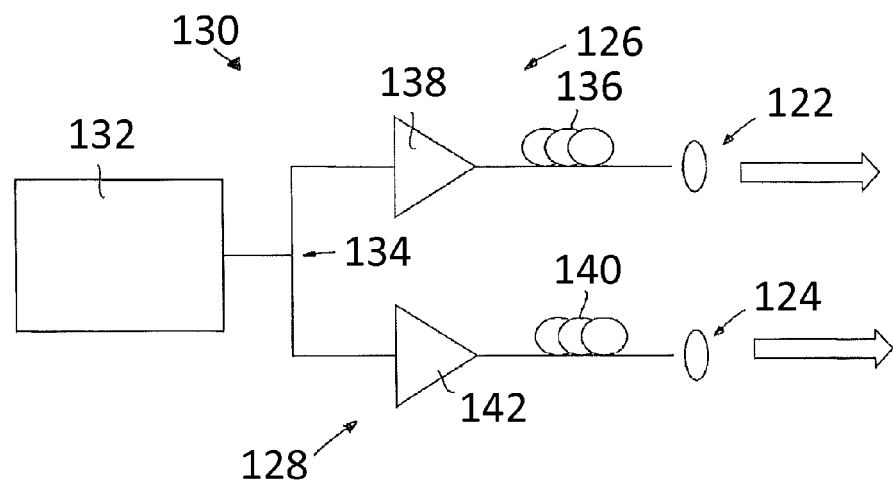
FIG. 9 is a schematic representation of a stimulated emission depletion microscopy optical source according to a tenth embodiment of the invention.

A tenth embodiment of the invention provides a STED microscopy optical source 130 as shown in FIG. 9. The STED microscopy optical source 130 of this embodiment is substantially the same as the STED microscopy optical source 120 of FIG. 8, with the following modifications. The same reference numbers are retained for corresponding features.

In this embodiment, the STED microscopy optical source 130 further comprises a pump optical source 132, which can comprise a pulsed pump optical source, and an optical splitter 134. The pump optical source is arranged to generate an optical signal at a pump wavelength. The optical splitter 134 is arranged to receive the optical signal and to split the optical signal into a first pump signal and a second pump signal.

The first optical source 126 comprises a first optical fibre 136, arranged to receive the first pump signal. In this example an optical amplifier 138 is provided between the optical splitter 134 and the optical fibre 136 in order to amplify the first pump signal, however it will be appreciated that the optical amplifier 138 is optional. The optical fibre 136 is arranged to cause the first pump signal to undergo spectral broadening on transmission through the fibre 136 to form an optical supercontinuum signal. In this example, the optical fibre 136 comprises an endlessly single mode nonlinear microstructured fibre, such as SC-5.0-1040 from NKT Photonics (Denmark) with a zero dispersion wavelength at approximately 1040 nm, having anomalous dispersion at the pump wavelength close to 1064 nm and the resulting optical supercontinuum pulse has a spectral range extending from approximately 500 nm to above 1.75 μm. The optical fibre 136 may alternatively comprise a tapered optical fibre or a tapered microstructured optical fibre such that supercontinuum is generated due to the nonlinear interaction with the pump signal with the fibre.

The second optical source 128 comprises a first microstructured optical fibre (MSF1) 140 arranged to receive the second pump signal. A second (optional) optical amplifier 142 is similarly provided between the optical splitter 134 and MSF1 140. MSF1 140 is arranged to cause the second pump signal to undergo four-wave mixing on transmission through the fibre 140 such that a first optical signal at a signal wavelength and a second optical signal at an idler wavelength are produced. In this example, MSF1 has a length of 1.5 meters, a hole diameter of 0.9 micrometers, a hole pitch of 3 micrometers, mode field diameter of approximately 5 micrometers and a zero dispersion wavelength of approximately 1103 nm.

In this example, the pump optical source comprises a passively mode locked fibre laser operating at a wavelength of between 1030 nm and 1080 nm at an 80 MHz pulse repetition rate. Individual pulses have a duration of between 80 ps and 200 ps. It will be appreciated that other pump optical sources may alternatively be used, operating at different wavelengths, and with different pulse durations and repetition rates.

With the pump optical source operating at 1064 nm, MSF1 generates a first optical signal at signal wavelength of approximately 742 nm and a second optical signal at an idler wavelength of approximately 1860 nm. Residual pump light at 1064 nm is also output from MSF1. the first optical signal, at 742 nm, is provided to the depletion signal output 124. This depletion signal output can be used to deplete several fluorescent dyes (with the corresponding excitation wavelength attained through filtration of the supercontinuum excitation output) including Pyradine 2/LDS 722 of Exciton Radiant dyes GmbH or RH 414 from Biotium Inc (excitation at 554 nm) or ATTO 633 and ATTO 647 nm of ATTO-TEC GmbH (Excitation at 630 nm to 635 nm) for example.

Figure 10:
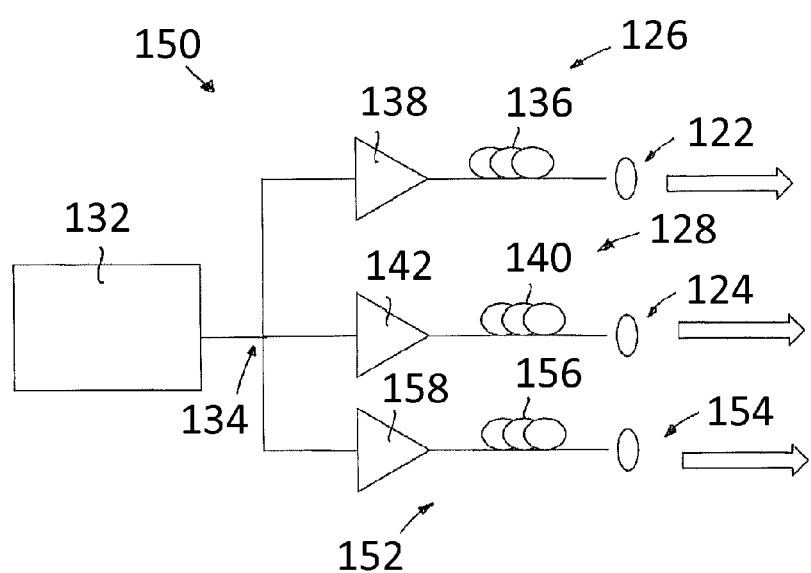
FIG. 10 is a schematic representation of a stimulated emission depletion microscopy optical source according to an eleventh embodiment of the invention.

FIG. 10 shows a STED microscopy optical source 150 according to an eleventh embodiment of the invention. The STED microscopy optical source 150 of this embodiment is substantially the same as the STED microscopy optical source 130 of FIG. 9, with the following modifications. The same reference numbers are retained for corresponding features.

In this embodiment, the STED microscopy optical source 150 comprises a further second optical source 152 and a second depletion signal output 154. The optical splitter 134 is arranged to split the optical signal into an excitation pump signal and two depletion pump signals. The second optical source 152 comprises a second microstructured optical fibre (MSF2) 156 arranged to receive a respective one of the two depletion pump signals. A third optical amplifier 158 is similarly (optionally) provided between the optical splitter 134 and MSF2 156. MSF2 156 is arranged to receive said respective depletion pump signal and to cause the received signal to undergo four-wave mixing on transmission through the fibre 156 to generate respective first and second optical signals. One of the first and second optical signals is provided to the second depletion signal output 154. MSF2 156 has different fibre parameters to MSF1 140, such that the signal wavelength of the first optical signal and the idler wavelength of the second optical signal generated in MSF2 156 are different to the signal and idler wavelengths of the first and second optical signals generated by MSF1 140.

In this example, MSF2 156 has a hole diameter of approximately 1.5 µm, a pitch of approximately 4.5 µm, a mode field diameter of approximately 5 µm, a length of 2 m and a zero dispersion wavelength of approximately 1145 nm. The second optical source 152 generates a first optical signal at a signal wavelength of 690 nm and a second optical signal at an idler wavelength 2230 nm when pumped at 1064 nm.

The STED microscopy optical source 150 may therefore be used to perform 2-colour STED imaging, enabling, for example, investigation of the spatial relationship of more than a single biomolecule at the nanoscale. The STED microscopy optical source 150 generates two depletion signal outputs at different, depletion wavelengths chosen to allow interrogation of particular fluorescent dyes used to label samples. The first depletion signal output, at approximately 742 nm, provides a source for stimulated emission of dyes including RH414 from Biotium Inc (excitation around 550 nm) or, if the spectral linewidth is large enough, this can be extended to achieve stimulated emission in dyes including ATTO 633 and ATTO 647N from ATTO-TEC GmbH (having excitation around 630 nm). Providing a second depletion signal at a wavelength of approximately 690 nm, enables the STED microscopy optical source 150 to also be used with dyes such as Alexa 594 from Invitrogen Corporation or ATTO 590 (excitation at 570 nm).

It will be appreciated that the number of second optical sources and depletion signal outputs may be increased to more than 2, in order to provide a larger number of depletion signal outputs. It will also be appreciated that the fibre parameters of MSF1 and MSF2 can be selected with flexibility in order to attain depletion signal outputs at various wavelengths.

Figure 11:
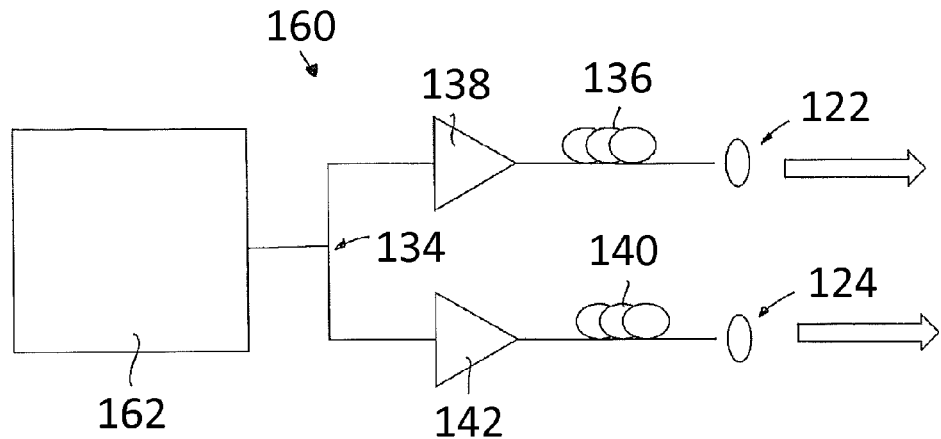
FIG. 11 is a schematic representation of a stimulated emission depletion microscopy optical source according to a twelfth embodiment of the invention.

A twelfth embodiment of the invention provides a STED microscopy optical source 160, as shown in FIG. 11. The STED microscopy source of this embodiment is substantially the same as the STED microscopy source 130 of FIG. 9, with the following modifications. The same reference numbers are retained for corresponding features.

In this embodiment, the pump optical source is a wavelength tuneable pump optical source arranged to generate an optical signal at one of a plurality of pump wavelengths. The pump wavelengths in this example lie within the spectral range 1020 nm and 1080 nm, enabling the STED microscopy optical source 160 to generate a depletion optical signal at a wavelength within the range 600 nm to 900 nm.

Figure 12:
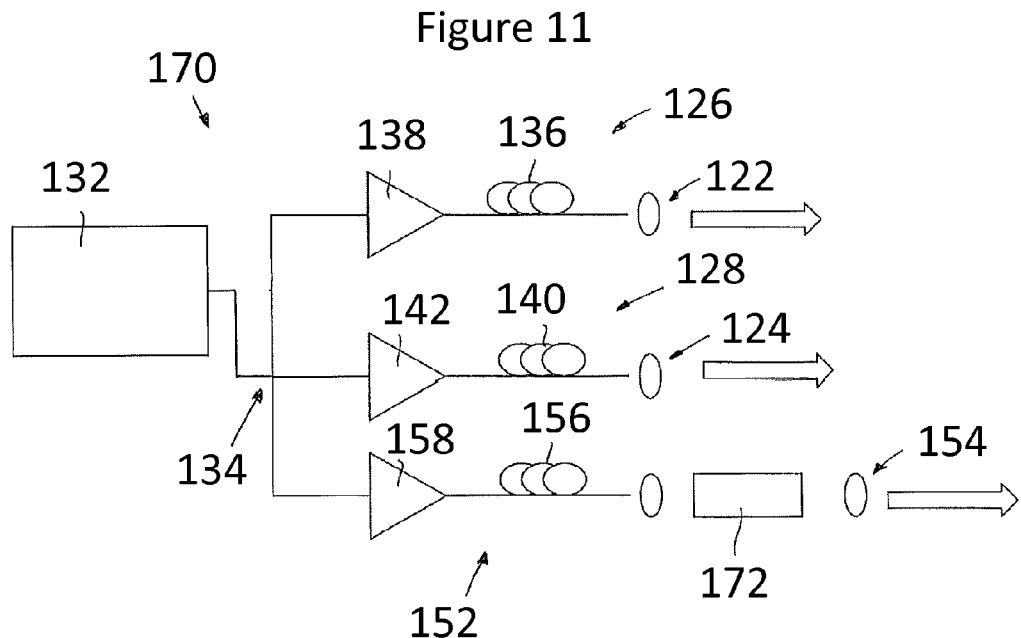
FIG. 12 is a schematic representation of a stimulated emission depletion microscopy optical source according to a thirteenth embodiment of the invention.

A STED microscopy optical source 170 according to a thirteenth embodiment of the invention is shown in FIG. 12. The STED microscopy optical source 170 is substantially the same as the STED microscopy optical source 150 of FIG. 10, with the following modifications. The same reference numbers are retained for corresponding features.

In this embodiment, the second optical source 152 further comprises a non-linear optical element 172, which in this example comprises a non-linear crystal such as a non-critically phased matched lithium triborate (LBO) crystal or a periodically-poled lithium niobate crystal (PPLN). The non-linear crystal 172 is arranged to receive the second optical signal at the idler wavelength from MSF3 156 and to cause the second optical signal to undergo second harmonic generation to form a frequency doubled output optical signal for delivery to the second depletion signal output 154.

In this example, the second optical signal from MSF2 156 has an idler wavelength of approximately 1200 nanometers, and the resulting frequency doubled output optical signal has a wavelength in the region of 600 nanometers. This is suitable to achieve stimulated emission in fluorescent dyes such as Yellow Fluorescent protein (YFP) with excitation in the 490 nm spectral range or Alexa Fluor 488 (excitation at 488 nm) for example. The inclusion of the non-linear optical crystal 172 therefore enables a depletion optical signal to the generated at lower wavelengths.

Figure 13:
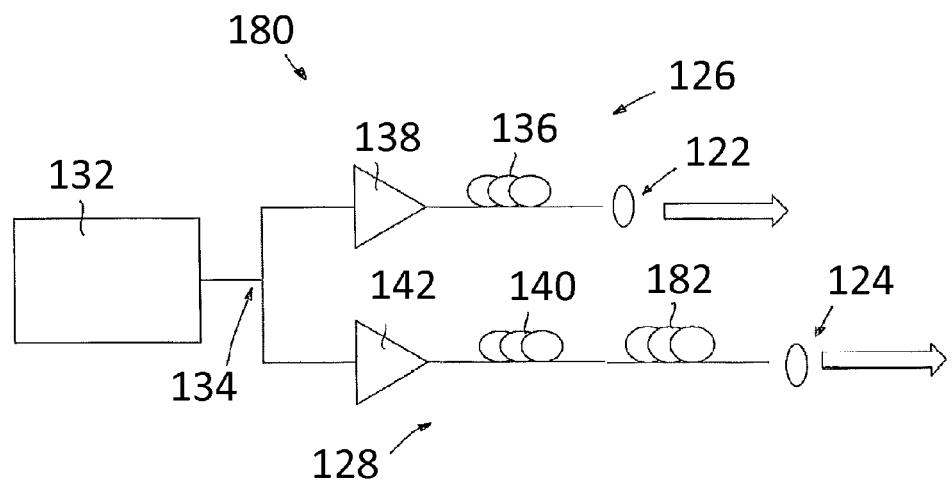
FIG. 13 is a schematic representation of a stimulated emission depletion microscopy optical source according to a fourteenth embodiment of the invention.

FIG. 13 shows a STED microscopy optical source 180 according to a fourteenth embodiment of the invention. The STED microscopy optical source 180 of this embodiment is substantially the same as the STED microscopy optical source 130 of FIG. 9, with the following modifications. The same reference numbers are retained for corresponding features.

In this embodiment, the second optical source 128 further comprises a second microstructured optical fibre (MSF2) 182. MSF2 182 is arranged to receive one of the first and second optical signals output from MSF1 140. MSF2 182 is arranged to cause one of the first and second optical signals to undergo four-wave mixing on transmission through the fibre 182 to generate a third optical signal at a second signal wavelength and a fourth optical signal at a second idler wavelength. By way of example, MSF1 and MSF2 are designed as a pair to produce a cascaded four-wave mixing signal in the red region of the spectrum (centred in the range from 595 nm to 600 nm) providing a suitable STED beam for imaging with YFP for example. In this example, MSF1 140 has a length of 1.0 meters, a hole diameter of 1.7 micrometers, a hole pitch of 2 micrometers, mode field diameter of approximately 2.2 micrometers and a zero dispersion wavelength of approximately 811 nm. The second depletion signal is therefore generated at a wavelength in the region of 742 nm.

Both one of the first and second optical signals and one of the third and fourth optical signals are provided to the optical output 124. In this example, the first optical signal and the third optical signal, at the first and second signal wavelengths, are selected. A singled depletion signal output comprising two wavelengths, each suitable for causing excitation of a different fluorophore in a different dye, is therefore generated.

It will be appreciated that there are numerous combinations of MSF fibre parameters which may be used to produce the desired wavelength through cascaded four-wave mixing process.

Figure 14:
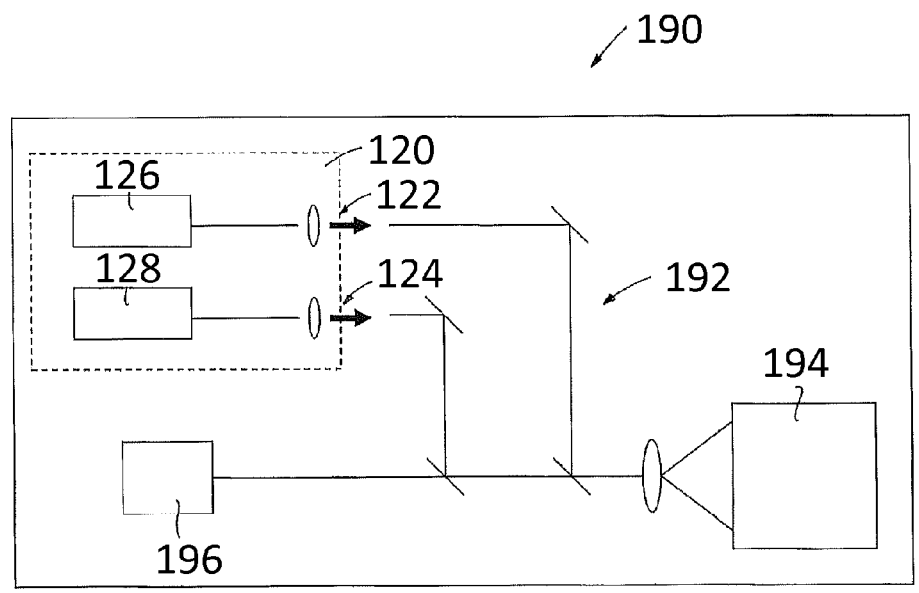
FIG. 14 is a schematic representation of a stimulated emission depletion microscope according to a fifteenth embodiment of the invention.

A fifteenth embodiment of the invention provides a STED microscope 190, as shown in FIG. 14.

The STED microscope 190 comprises a STED microscopy optical source according to any of embodiments nine to sixteen. The STED microscopy optical source 120 of FIG. 8 is shown here but it will be appreciated that any of the other STED microscopy optical sources described above may alternatively be used.

For illustration only, FIG. 14 also shows typical parts of a STED microscope 190, which do not form part of this embodiment, including beam guiding optics 120 arranged to deliver the excitation signal from the excitation signal output 122 and the depletion signal from the depletion signal output 124 of the STED microscopy optical source 120 to a sample area 194. The beam guiding optics 120 are also arranged to deliver stimulated emission signals generated from a sample within the sample area 194 to an optical detector 196. The structure and operation of a STED microscope will be well known to the person skilled in the art.

Figure 15:
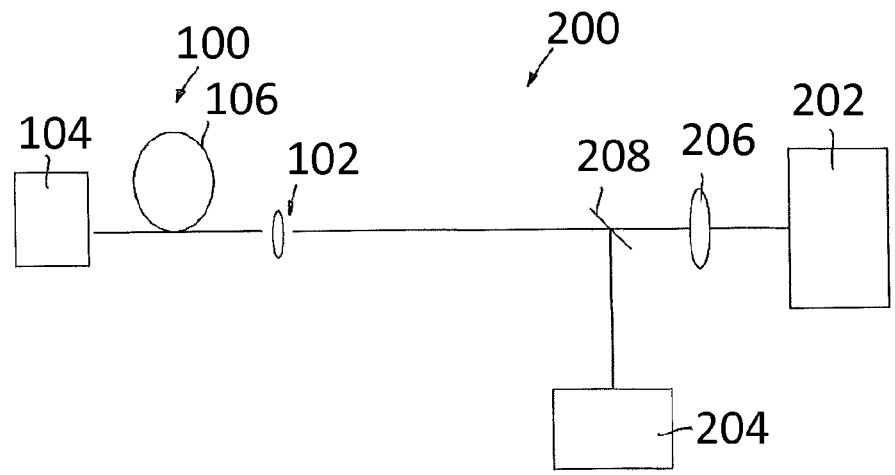
FIG. 15 is a schematic representation of fluorescence imaging apparatus according to a sixteenth embodiment of the invention.

FIG. 15 shows fluorescence imaging apparatus 200 according to a sixteenth embodiment of the invention. The apparatus 200 comprises a wavelength tuneable optical source 100 as shown in FIG. 6. It will be appreciated that the visible light optical source 110 of FIG. 7 may alternatively be used.

For illustration only, FIG. 15 also shows typical parts of a fluorescence imaging apparatus, which do not form part of this embodiment, including a sample area 202 in which a sample to be imaged is located, optical detection apparatus 204, a lens 206 and a dichroic mirror 208. The structure and operation of fluorescence imaging apparatus will be well known to the person skilled in the art. Fluorescence imaging apparatus", as used herein, includes, by way of example, within its ambit a flow cytometer, a confocal microscope and a STED microscope. As one ordinary skill in the art can readily appreciate, the fluorescence imaging apparatus shown in FIG. 15 is exemplary. Not all features shown in FIG. 15 are necessarily included in all instances of a fluorescence imaging apparatus, and a fluorescence imaging apparatus can comprise features not necessarily shown in FIG. 15.

Figure 16:
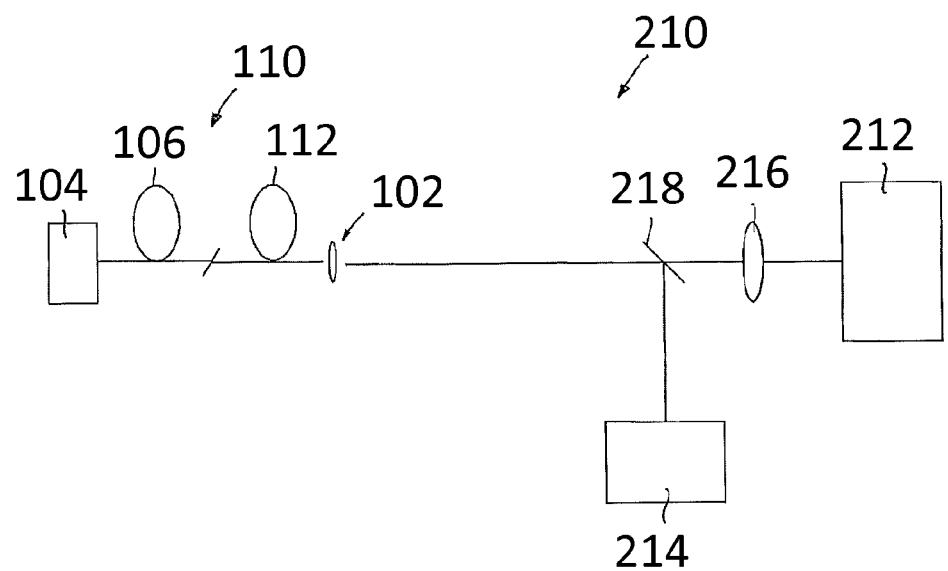
FIG. 16 is a schematic representation of a confocal microscope according to a seventeenth embodiment of the invention.

FIG. 16 shows a confocal microscope 210 according to a seventeenth embodiment of the invention. The confocal microscope 210 comprises a visible light optical source 110, according to the eighth embodiment of the invention as described above in relation to FIG. 7. FIG. 16 also shows typical parts of a confocal microscope 210, which do not form part of the embodiment, including a sample area 212 in which a sample to be imaged is located, optical detection apparatus 214, and beam steering optics in the form of a lens 216 and a dichroic mirror 218. The structure and operation of a confocal microscope will be well known to the person skilled in the art.

Figure 17:
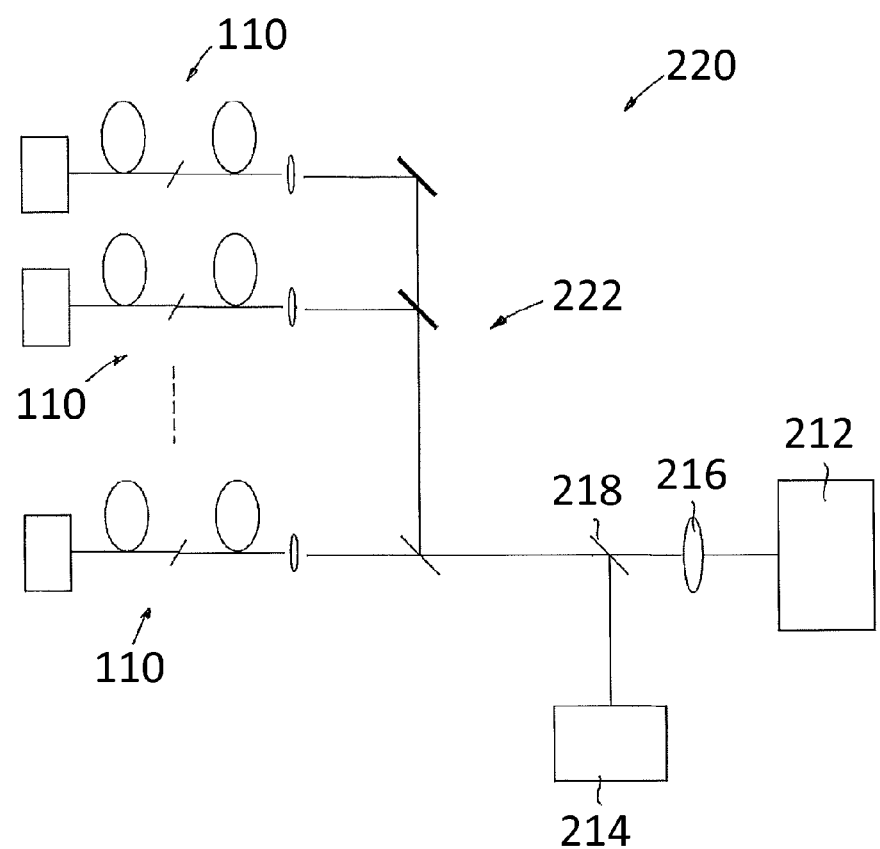
FIG. 17 is a schematic representation of a confocal microscope according to an eighteenth embodiment of the invention.

FIG. 17 shows a confocal microscope 220 according to an eighteenth embodiment of the invention. The confocal microscope 220 is substantially the same as the microscope 210 of FIG. 16, with the following modifications. The same reference numbers are retained for corresponding features.

In this embodiment, the confocal microscope 220 comprises a plurality of visible light optical sources 110, each arranged to generate an optical signal at a different wavelength. The microscope 220 further comprises beam steering and combining optics 222 arranged to direct the optical signals from each optical source 110 to the sample area 212.

As with the fluorescence imaging apparatus described above in FIG. 15, the confocal microscopes 210 shown in FIGS. 16 and 17 above are exemplary, and the considerations noted above in conjunction with the fluorescence imaging apparatus regarding such non-limiting exemplary illustrations apply equally here.

Figure 18:
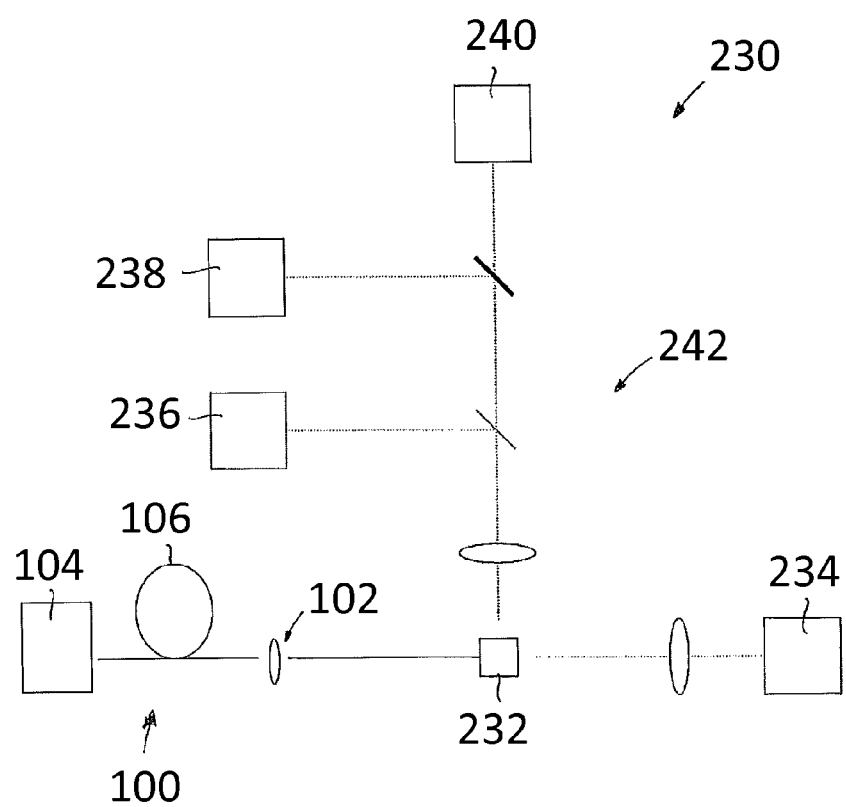
FIG. 18 is a schematic representation of a flow cytometer according to a nineteenth embodiment of the invention.

A nineteenth embodiment of the invention provides a flow cytometer 230 as shown in FIG. 18. The flow cytometer 230 comprises a wavelength tuneable optical source 100 as shown in FIG. 6. It will be appreciated that the visible light optical source 110 of FIG. 7 may alternatively be used.

For illustration only, FIG. 18 further shows typical parts of a flow cytometer, which do not form part of the embodiment, including a sample area 232, a forward scatter detector 234, a side scatter detector 236, a first fluorescence detector 238 and a second fluorescence detector 240. Beam steering optics 242 are also shown. The structure and operation of a flow cytometer will be well know to the person skilled in the art.

Figure 19:
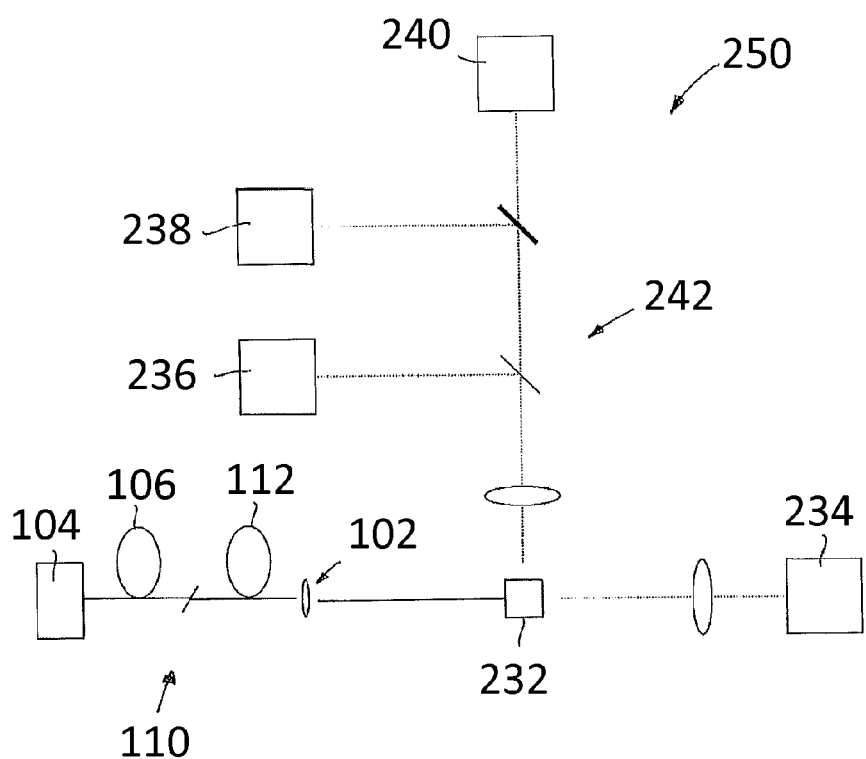
FIG. 19 is a schematic representation of a flow cytometer according to a twentieth embodiment of the invention.

FIG. 19 shows a flow cytometer 250 according to a twentieth embodiment of the invention. The flow cytometer 250 is substantially the same as the flow cytometer 230 of FIG. 18, with the following modifications.

In this example, the flow cytometer 250 comprises a visible light optical source 110 as shown in FIG. 7.

Figure 20:
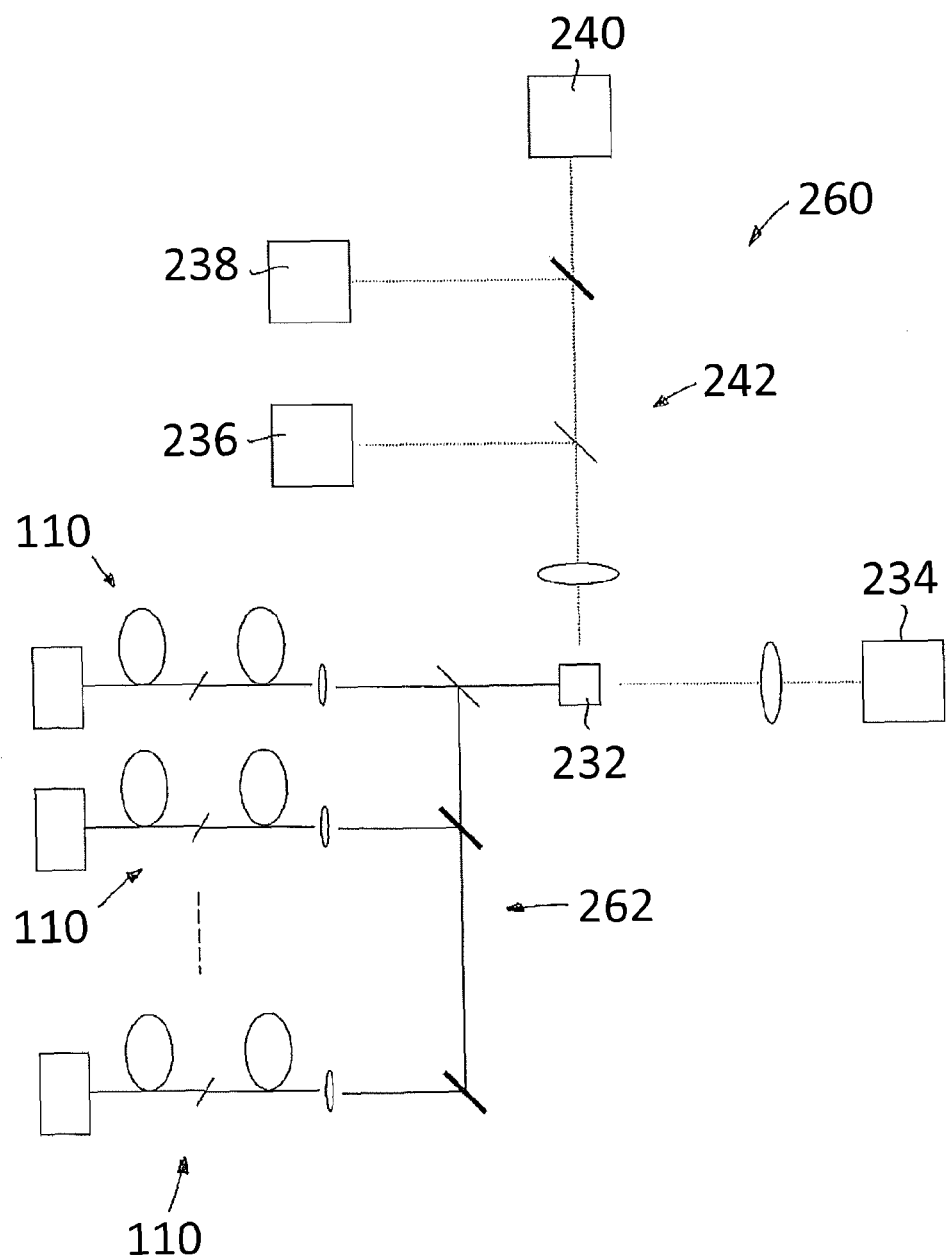
FIG. 20 is a schematic representation of a flow cytometer according to a twenty-first embodiment of the invention.

A flow cytometer 260 according to a twenty-first embodiment of the invention is shown in FIG. 20. The flow cytometer 260 of this embodiment is substantially the same as the flow cytometer 250 of FIG. 19, with the following modifications. The same reference numbers are retained for corresponding features.

In this embodiment, the flow cytometer 260 comprises a plurality of visible light optical sources 110 and is further provided with beam steering optics 262 arranged to direct the optical signals from each optical source 110 to the sample area 232.

The illustrations of the flow cytometers shown above are exemplary, as explained above in conjunction with the description of typical fluorescence imaging apparatus.

Figure 21:
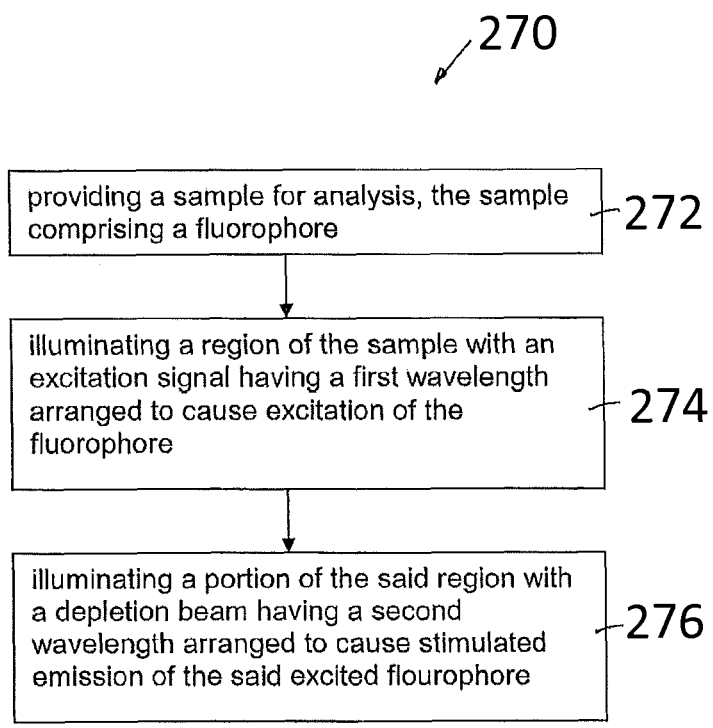
FIG. 21 shows the steps of a method of performing stimulated emission depletion, STED, microscopy, according to a twenty-second embodiment of the invention.

A twenty-second embodiment of the invention provides a method 270 of performing stimulated emission depletion (STED) microscopy, as shown in FIG. 21.

The method 270 comprises:
  providing a sample for analysis, the sample comprising a fluorophore 272;
  illuminating a region of the sample with an excitation signal having a first wavelength arranged to cause excitation of the fluorophore 274; and
  illumination a portion of the said region with a depletion beam having a second wavelength arranged to cause stimulated emission of the said excited fluorophore 276.

At least part of one of the deletion signal and the excitation signal is generated by a first non-linear optical process. At least part of the other of the depletion signal and the excitation signal is generated by a second non-linear optical process which is different to the first non-linear optical process.

In a further embodiment the first non-linear optical process generates an optical supercontinuum signal and the second non-linear optical process comprises a four-wave mixing process. The excitation signal is generated by the first non-linear optical process and the depletion signal is generated by the second non-linear optical process.

In a further embodiment, the sample comprises a second fluorophore and the method further comprises:

illuminating the region of the sample with an excitation signal having a third wavelength arranged to cause excitation of the second fluorophore; and illuminating a portion of the said region with a second depletion beam having a third wavelength arranged to cause stimulated emission of the said excited second fluorophore.

Figure 22:
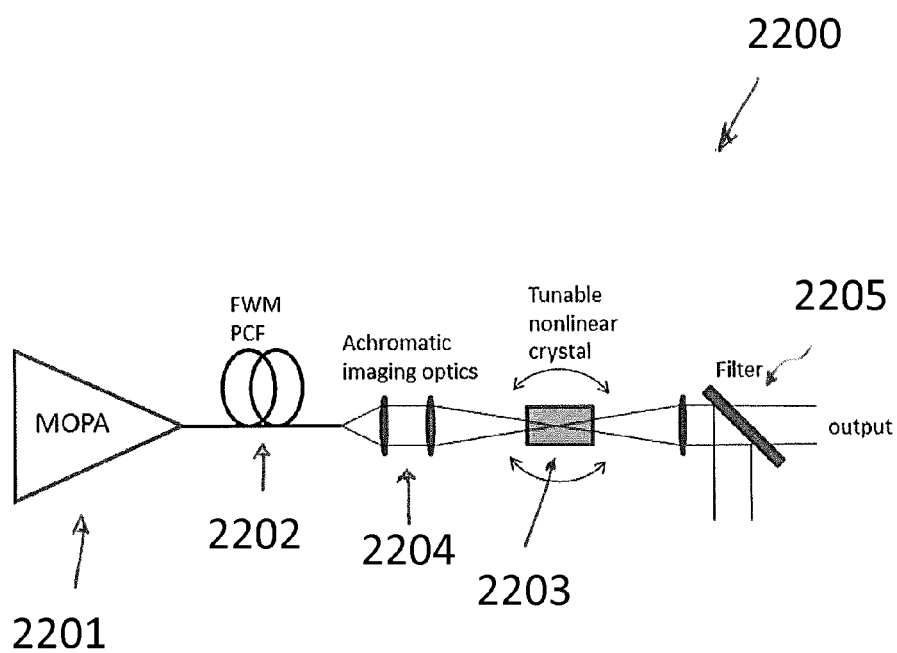
FIG. 22 shows a frequency conversion arrangement.

A frequency conversion arrangement 2200 according to a twenty third embodiment is shown in FIG. 22. As shown, the frequency conversion arrangement includes a pump optical source 2201 in the form of a Master Oscillator Power Amplifier (MOPA) system, and a microstructured optical fibre 2202. The MOPA can include one or more ytterbium doped fibre amplifiers. The frequency conversion arrangement further comprises a nonlinear optical element 2203 in the form of a nonlinear crystal.

The MOPA system of FIG. 22 is operable to generate a first optical signal comprising picosecond (e.g: 80 ps) optical pulses at a pump wavelength which can be tunable (e.g: tunable between 1030 to 1080 nm). Alternatively, a fixed wavelength system may be used. The microstructured optical fibre 2202 is spliced to the output of the MOPA system so as to receive the first optical signal from the MOPA. The microstructured fibre 2202 has a normal dispersion at the pump wavelength. The microstructured fibre 2202 is arranged to cause the pulses to undergo four-wave mixing on transmission through the fibre 2202 so as to generate a second optical signal at a signal wavelength and a third optical signal at an idler wavelength. The first optical signal is depleted by this process, but a residual first optical signal remains at the output of the fibre 2202.

The residual first optical signal, the second optical signal and the third optical signal emerge from the microstructured fibre 2202 and are focussed together into the nonlinear crystal 2203 by way of coupling optics 2204.

As shown, coupling optics 2204 includes a collimating lens and a focussing lens having a suitable focal length (e.g: 8 mm and 40 mm respectively).

Coupling optics 2204 may comprise non-achromatic lenses. However, for non-achromatic lenses, the focal length depends on the wavelength of light and therefore coupling efficiency into the fibre 2202 may be affected by chromatic aberration.

Preferably, coupling optics 2204 comprises an achromatic imaging system, for example comprising achromatic lenses or a system of lenses which compensates for chromatic aberration. This allows improved coupling into the fibre 2202, particularly because the three beams have excellent spatial and temporal overlap, the same polarisation state and good beam quality.

In the example of FIG. 22, the nonlinear element 2203 comprises an 8 mm long BBO crystal cut for type I (o+o→e) critical phase matching. However, the nonlinear element may alternatively comprise another crystal or nonlinear device adapted for critical phase matching, for example LBO or BiBO. As an alternative to critical phase matching, a suitable quasiphase matching element (e.g: PPLN, PPKTP, PPLT) may be used. Alternatively, or in addition, the nonlinear element may comprise a plurality of the same or different crystals and/or other suitable nonlinear generation means.

The BBO crystal 2203 may be tuned by changing the orientation of the crystal, e.g: by rotating the crystal with respect to the angle of the input optical signals by up to around 20 degrees in the phase matching plane. Where a quasiphase matching element is employed, the element may be tuned with temperature or fan-out-grating tuning.

As shown, one or more filters 2205 may be employed at the output of the crystal to select a spectral region of interest (e.g all visible wavelengths), and to block or divert regions which may not be of interest in particular cases, e.g: infrared wavelengths. A short pass filter with a cut-off at 700 nm is preferred for visible output, but in other cases other filters may alternatively or in addition be used to limit the crystal output to spectral regions of interest.

By tuning the crystal 2203, different frequency conversion options may be selected. FIGS. 23(a) to 23(d) show spectra which can generated at different orientations of the crystal. In each of the examples shown in FIGS. 23(a) to 23(d), the pump wavelength is 1066 nm and the four-wave mixing signal wavelength is 868 nm.

Figure 23:
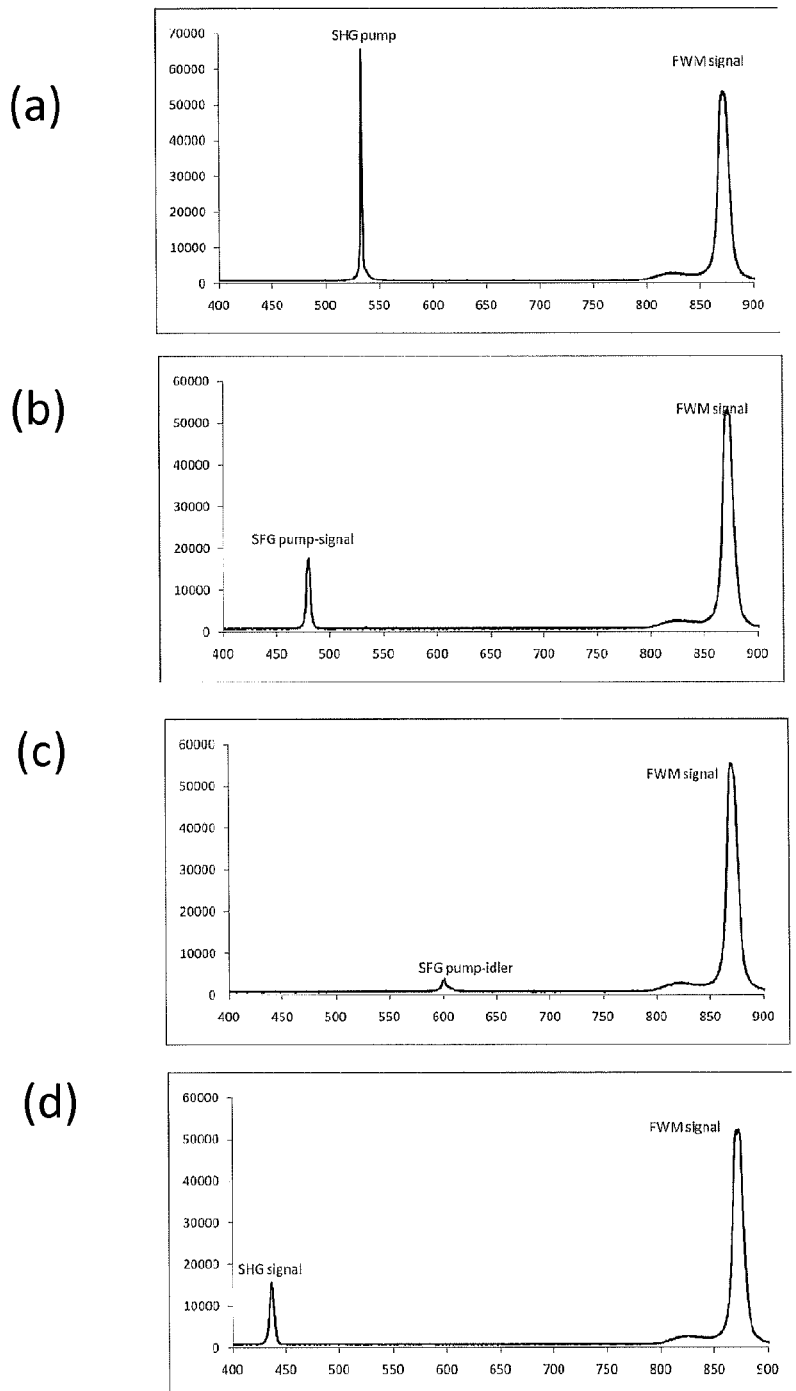
FIG. 23 illustrates output spectra in different frequency conversion modes of the frequency conversion arrangement.

As illustrated in FIG. 23(a), the crystal can be tuned to satisfy a phase condition for second harmonic generation (SHG) of the pump wavelength. In this way, the first optical signal is caused to undergo second harmonic generation on transmission through the crystal. FIG. 23(a) shows a measured spectrum in this particular frequency conversion mode. The spectrum shows the presence of the second harmonic of the pump wavelength at 533 nm.

The crystal is tuneable to select other modes of operation in which other phase conditions are met, thereby to generate different optical signals at different frequency-converted wavelengths.

For example, the crystal may be tuned to satisfy a phase condition for sum frequency generation (SFG) of the pump and signal wavelengths. In this case, the first and second optical signals are caused to undergo sum frequency generation on transmission through the crystal. FIG. 23(b) shows a measured spectrum for this case.

The crystal may alternatively be tuned to satisfy a phase condition for sum frequency generation of the pump and idler wavelengths. In this case, the first and third optical signals are caused to undergo sum frequency generation on transmission through the crystal. FIG. 23(c) shows a measured spectrum for this case.

The crystal may alternatively be tuned to satisfy a phase condition for second harmonic generation of the signal wavelength. In this frequency conversion mode, the second optical signal is caused to undergo second harmonic generation on transmission through the crystal. FIG. 23(d) shows a measured spectrum for this case.

Further frequency conversion processes may also be initiated by appropriately tuning the angle of the crystal. For example difference frequency generation (DFG) of the pump and idler wavelengths, difference frequency generation of the signal and pump wavelengths and difference frequency generation of the signal and idler wavelengths may be initiated by selectively tuning the crystal.

At some angles of the crystal, a phase condition for more than one nonlinear process may be met. Accordingly at some crystal orientations, one or more of the first, second and third signals may be caused to undergo two (or more) nonlinear process on transmission through the nonlinear element such that two or more frequency-converted optical signals are generated. For example phase matching for SHG of the pump wavelength may coincide with DFG of the pump and idler wavelengths.

The frequency converted wavelengths for the nonlinear processes discussed above may be determined using the following equations, which are well known per se to those skilled in the art:

SHG of Pump, Signal, Idler:

$$\omega_{SHG\,pump}=2\omega_p; \omega_{SHG\,signal}=2\omega_s; \omega_{SHG\,idler}=2\omega_i$$

SFG of Pump and Signal:

$$\omega_{SHG\,pump}=\omega_p+\omega_s$$

SFG of Pump and Idler:

$$\omega_{SHG\,pump\,idler}=\omega_p+\omega_s$$

DFG Pump—Idler $$\omega_{DFG\,pump\,idler}=\omega_p-\omega_i$$

DFG Signal—Pump $$\omega_{DFG\,signal\,pump}=\omega_s-\omega_p$$

DFG Signal—Idler $$\omega_{DFG\,signal\,idler}=\omega_s-\omega_i$$

As will be understood by those skilled in the art, in these equations the conventional symbol w refers to angular frequency, from which the corresponding wavelength may be calculated.

Different wavelengths can be produced at the output of the frequency conversion arrangement 2200 by selecting different pump wavelengths of the MOPA 2201 and tuning the crystal to select a desired frequency conversion mode. When the MOPA wavelength is tuned to a new wavelength, the four-wave mixing signal and idler wavelengths also change so as to meet the four-wave mixing phase-matching condition. Nonlinear processes can then be selectively initiated for the new wavelength by appropriately adjusting the crystal angle as discussed above. In this way, a very broad tuning range can be obtained by the frequency conversion arrangement 2200.

An example of possible tuning ranges is shown in the following table:

|  | minimum wavelength (nm) | maximum wavelength (nm) |
| --- | --- | --- |
| Pump | 1047 | 1072 |
| FWM signal | 743 | 876 |
| FWM idler | 1381 | 1771 |
| SHG idler | 690 | 886 |
| SHG pump | 523 | 536 |
| SHG signal | 371 | 438 |
| SFG pump - signal | 434 | 482 |
| SFG pump- idler | 603 | 657 |
| DFG signal-pump | 2560 | 4791 |
| DFG signal-idler | 1280 | 2395 |

The tuning ranges in the table above can be obtained for a microstructured fibre having a zero dispersion wavelength at 1071 nm. It will be appreciated that different ranges can be produced by providing a different microstructured fibre or a different MOPA tuning wavelength.

Although FIG. 22, illustrates a MOPA-based configuration for pumping the nonlinear crystal 2203, alternatively other suitable optical sources may be used to pump the crystal 2203. For example, residual pump light may emerge from the microstructured optical source of FIG. 1 and this residual pump light may be coupled into the nonlinear crystal 2203 along with the signal and/or idler wavelengths generated in the microstructured optical fibre 20. The nonlinear crystal 2203 may then be tuned as described above to select one of a plurality of frequency conversion modes in which one or more of said received signals are caused to undergo a nonlinear process on transmission through the nonlinear element such that a frequency-converted optical signal is generated. Alternatively signals generated in any of the optical sources described above with reference to any of FIGS. 2-7 may be used to pump the nonlinear element 2203. As noted above, it can be particularly advantageous that the MOPA or other source employed have a tunable output signal or signals.

Furthermore, although the optical signals at the pump wavelength, the signal wavelength and the idler wavelength may be coupled into the nonlinear crystal, in some examples only a selected two of these three optical signals are coupled into the nonlinear crystal. This may for example be achieved by selectively filtering out one of the pump, signal and idler wavelengths after the fibre 2202 output and before the coupling optics 2204.

Still further, although the frequency conversion arrangement of FIG. 22 shows a single microstructured fiber, alternatively frequency-converted light generated by four wave mixing in a microstructured fiber cascade may be coupled into the crystal. Light generated in different stages of the cascade may be coupled into the crystal, in which case the number of different wavelengths coupled into the crystal may exceed three.

According to a twenty fourth embodiment there is provided a Coherent Anti Stokes Raman Scattering (CARS) imaging method. CARS microscopy comprises an imaging technique that can be based on the vibrational frequency of molecules. For example, in a CARS imaging microscopy technique, two laser signals, typically in the form of picosecond laser pulses, are delivered to the sample to be imaged. Suitable picosecond pulses include pulses having a range from 1 ps to 10 ps; 1 ps to 25 ps; 1 ps to 50 ps; or 1 ps to 100 ps. For the purposes of the present discussion, the pulses can be referred to as a CARS pump pulse and a Stokes pulse. The two laser signal can be delivered so as to overlap, in one or both of space and time, on the sample.

Consider the CARS pump to have a wavelength $\lambda_C$ and a corresponding frequency $\omega_C$, and the Stokes signal to have a wavelength $\lambda_S$ and a corresponding frequency $\omega_S$. The CARS pump and Stokes signals can yield a beat frequency $\omega_C-\omega_S$ that is, as the equation indicates, the difference between the frequency of the CARS pump and Stokes signals. This beat frequency can induce vibrations of a molecule at the beat frequency. The excitation of these vibrations is often most effective if the beat frequency $\omega_C-\omega_S$ is substantially equal to the characteristic Raman frequency $\Omega$ of the particular molecule it is desired to image. Often the relative difference $\omega_C-\omega_S$ frequencies between the CARS pump and Stokes signals is more important that the actual values of the wavelengths $\lambda_C$ or $\lambda_S$, although typically near infrared wavelengths can offer greater penetration depths within samples, which is can be desirable in imaging. When the frequency difference approaches the frequency of a specimen's molecular vibration, a strong, blue-shifted anti-Stokes signal is generated, which can be detected, allowing molecule-specific imaging. A particular molecule in a sample can be imaged by selecting a beat frequency tailored to the that target molecule, and different molecules in a sample can be imaged by changing the beat frequency, such as, for example, by changing one or both frequencies of the CARS pump signal or of the Stokes signal.

Four wave mixing (FWM) processes, such as those described in the various embodiments disclosed herein, are interesting in that 3 signals can be involved—the pump, the signal and the idler, and thus more than one pair can be used to form a desired beat frequency signal at the sample for imaging. For example, the FWM pump can be delivered to the sample as the CARS pump and the FWM idler as the Stokes signal, or, alternatively, the FWM signal can be delivered as the CARS pump and the FWM pump as the Stokes signal. One of ordinary skill will readily ascertain, from the disclosure herein, that other pairs can be used as well to form a beat frequency for a CARS imaging method according to the present invention. For example, the FWM signal and FWM pump could be used.

The FWM mixing processes can be additionally interesting for another reason as well. The tuning response of the idler and FWM signal to a change in the pump wavelength can be such that difference frequency between a selected pair (e.g., between FWM pump and idler) will change as the pump wavelength changes. A wide range of beat frequencies can be thus provided by tuning the FWM pump, and this range is enhanced in that there are different pairs to choose from, as noted above. By tuning the MOPA output wavelength in the embodiments of signal sources shown above, the difference frequency generated between means that it is possible to scan the difference frequency wavenumber (inverse of wavelength) to match the vibrational frequency of molecules within a sample under CARS imaging investigation.

It is also noted that as the wavelength of the FWM pump is varied, the wavelength of the idler and signal can change by different amounts. For example, as described in more detail below, in one instance tuning the pump wavelength by 32 nm results in a signal tuning range of 140 nm and an idler tuning range of more than 400 nm. This can further enhance the tuning range of available beat frequencies for CARS imaging.

There are other degrees of freedom as well for providing a particular beat frequency or range of beat frequencies. The FWM process typically takes place, as disclosed herein, within a microstructured fiber. The zero dispersion wavelength of the microstructured fiber can be varied by varying one or more of the design parameters of the fibre (e.g., core size, pitch of the longitudinally extending holes, ratio of hole diameter to pith (d/A), air fill fraction, etc.), and varying the zero dispersion wavelength can provide a different ranges for the wavelengths of FWM signal and idler generation that are obtained responsive to the variation of the FWM pump.

Figure 25:
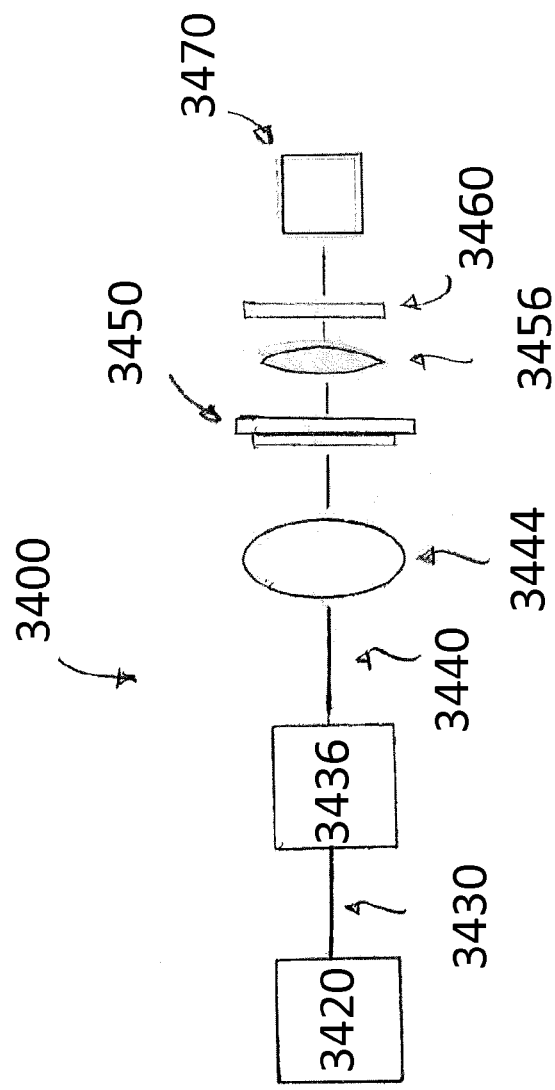
FIG. 25 shows a Coherent Anti Stokes Raman Scattering (CARS) imaging apparatus.

One of ordinary skill in the art, upon study of the present disclosure, will realize that any source or source assembly described herein, whether described as a source alone or as part of an apparatus (e.g., STED microscope), that can generates more than one signal such that a beat or difference frequency may be produced between the signals, can be suitable in appropriate circumstances for the practice of the CARS imaging method or as part of the CARS imaging apparatus described herein (e.g., see FIG. 25, described below). If elsewhere herein one of the signals desired for CARS is described as being produced internally to a source, one of ordinary skill, cognizant of the present disclosure, will understand that it is appropriate to deliver the signal to the CARS process such that the sample is exposed to the beat frequency. One or both of the CARS pump and Stokes signals can be generated by a nonlinear process, such as FWM process, or as part of harmonic generation, such as, for example second harmonic generation (SHG), or a part of sum frequency generation or difference frequency generation in a nonlinear element such as, for example, a crystal or a wavelength converter. A signal can be a residual of the pump for a FWM process, As one illustrative example, the following discussion will consider the sixth embodiment of the invention, which is shown in FIG. 6, in which a microstructured or photonic crystal fiber is pumped for FWM by a tunable wavelength pulsed MOPA. With further reference to FIG. 6, a tunable MOPA (104) with wavelength tunability from 1055 nm to 1080 nm, can produce tunable pump, signal and idler wavelengths at the output (102) of the PCF (106). Tuning the MOPA wavelength from 1055 nm to 1080 nm resulted (for a specific PCF with a zero dispersion wavelength of approximately 1103 nm) in a tunable signal pulse with wavelength from 720 nm to 809 nm and a corresponding tunable idler wavelength from approximately 2250 nm to 1100 nm. In one experiment, the tuning range was extended. The pump MOPA wavelength was tuned from approximately 1035 nm to 1080 nm (a broader range than described below but still within the Yb-doped fibre gain bandwidth range of approximately 1020 nm to 1100 nm).

Figure 24:
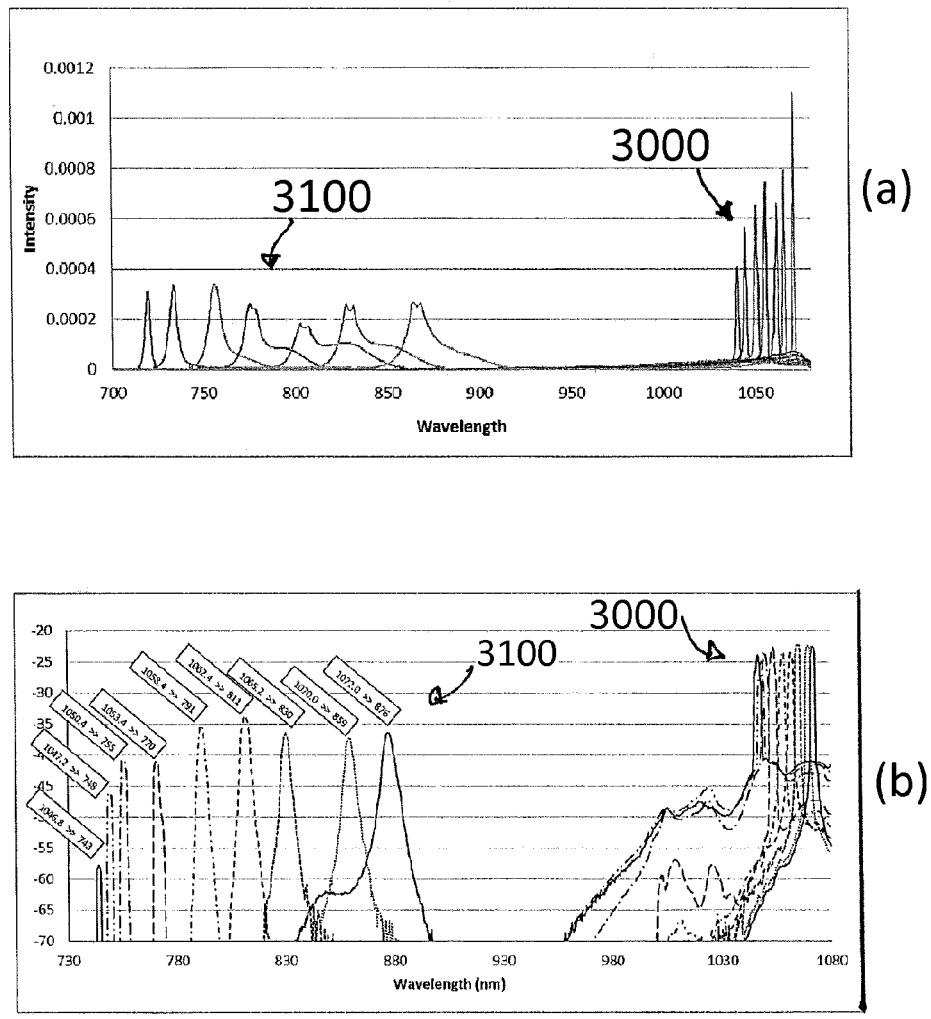
FIG. 24 illustrates spectra obtained in an experiment.

This particular experiment provided the spectra shown in FIG. 24. FIGS. 24(a) and 24(b) differ slightly in that FIG. 24(a) is plotted using a linear vertical scale and FIG. 24 (b) is plotted using a log scale, and in that different pump power levels were used. With reference to FIGS. 24(a) and (b), the FWM pump, indicated by reference numeral 3000 was tuned from approximately 1040 nm to approximately 1072 nm, resulting in a signal, indicated by reference number 3100, tuned from approximately 719 nm to approximately 876 nm). The corresponding idler wavelength (not shown) is tunable from approximately 1800 nm to 1380 nm over this range of MOPA FWM pump wavelengths. Tuning the pump wavelength by 32 nm results in a signal tuning range of 140 nm and an idler tuning range of more than 400 nm. For the upper plot, FIG. 24(a), the FWM pump average power was about 3 Watts, resulting in a FWM signal average power of about 1 Watt. For the lower plot, FIG. 24(b), the FWM pump average power was in the range of 8-10 Watts, resulting in a FWM signal average power of about 5 Watts.

Table I below illustrates, for the particular FWM process example given above, some of the beat frequencies that may be obtained when the FWM pump is tuned from 1046 nm to 1072 nm for beat frequencies using two of the different pairs of the available candidates (FWM pump, signal and idler) in an FWM process. The pairs shown in Table I for producing a beat frequency are (a) the FWM pump and FWM signal and (b) the FWM signal and the FWM idler. A representative CARS signal that could be representative of the response of a sample is also provided in Table 1.

It is noted that there the difference frequency for using the FWM pump as the CARS pump and the FWM idler as the Stokes is the same as for using the FWM signal as the CARS pump and the FWM pump as the Stokes. Thus there can be an advantage, where a FWM source is used, to deliver all three signals to the sample, as this may enhance the strength of the CARS blue shifted signal that is imaged, as there can be an increased strength of the frequency difference signal.

TABLE I

| FWM CARS laser | | | FWM signal - FWM pump OR FWM pump - FWM idler | | | FWM signal - FWM idler | | |
|---|---|---|---|---|---|---|---|---|
| FWM pump (nm) | FWM signal (nm) | FWM Idler (nm) | Difference (e.g., FWM signal - FWM pump) (nm) | Difference frequency wavenumber (cm-1) | Blue-shifted CARS signal (nm) | Difference (e.g., FWM signal - FWM idler) (nm) | Difference frequency wavenumber (cm-1) | Blue Shifted CARS signal (nm) |
| 1046 | 743 | 1771 | 2560 | 3906 | 576 | 1280 | 7812 | 470 |
| 1047 | 748 | 1745 | 2618 | 3820 | 582 | 1309 | 7639 | 476 |
| 1050 | 755 | 1726 | 2685 | 3725 | 589 | 1342 | 7450 | 483 |
| 1054 | 770 | 1668 | 2861 | 3496 | 607 | 1430 | 6991 | 501 |
| 1058 | 791 | 1599 | 3131 | 3194 | 631 | 1565 | 6388 | 525 |
| 1062 | 811 | 1540 | 3427 | 2918 | 656 | 1714 | 5836 | 550 |
| 1065 | 830 | 1486 | 3759 | 2660 | 680 | 1879 | 5321 | 576 |
| 1070 | 859 | 1418 | 4356 | 2296 | 718 | 2178 | 4591 | 616 |
| 1072 | 876 | 1381 | 4791 | 2087 | 741 | 2396 | 4174 | 641 |

The FWM efficiency can be higher than 25%, and the pump power delivered by the tunable wavelength MOPA can be, in certain practices of the invention, scalable to greater than 20 Watts, resulting in signal and idler powers of more than 5 Watts. Alternatively, due to the efficiency of this process, lower powers can be delivered by an ultra-compact and low-complexity laser source.

According to a twenty fifth embodiment there is provided a CARS microscope. FIG. 25 schematically illustrates a CARS microscope 3400 for performing CARS imaging. Not all features that can be included in such a microscope are necessarily shown in FIG. 25, nor are all the features shown in FIG. 25 necessarily part of all CARS microscopes. CARS microscope 3400 includes an optical source 3420. Optical source 3420 may comprise the optical source described above with reference to FIG. 6, with the wavelength tuning range extended as discussed above. Alternatively, the optical source 3420 may comprise any of the optical sources described above with reference to FIGS. 1 to 7 and/or the frequency conversion arrangement described above with reference to FIG. 22.

The optical source can provide, such as along optical path 3430, at least two signals for providing an appropriate difference frequency signal for facilitating the CARS imaging process. The CARS microscope 3400 can further include a scanner 3426 optically downstream of the source 3420 for providing scanned signals along free space optical path 3440 to the objective assembly 3444, which optical conditions the signals before delivery of the signals to the target sample 3450. Optic 3456 and optical filter 3460 can condition the CARS signal generated responsive to the aforementioned difference frequency before detection of the CARS signal by the detector 3470. As noted above, one or more of the signals provided by the optical source 3420 can be tunable over wavelength (which, as one of ordinary skill readily appreciates) equivalently means tunable over frequency.

It is typically desirable that one or all of the signals that are used in CARS (e.g., as the CARS pump or Stokes signal) to generate the difference frequency be relatively narrowband. The use of narrowband pulses can promote better imaging resolution. For this reason pulses have a picosecond duration can be preferable to femtosecond pulses, as the picosecond pulse can have a smaller bandwidth associated therewith. However, MOPA assemblies that include ytterbium fibre amplifiers that amplify picosecond pulses often spectrally broaden the signals they amplify. Pulsed ytterbium amplifiers producing pulse widths in certain range (e.g., 1 ps to 50 ps; 1 ps to 100 ps; or 1 ps to 200 ps) can often spectrally broaden the pulses, typically due primarily to self phase modulation along the amplifier fibre. The amplified signals can have a bandwidth, for example, of greater than 10 nm; greater than 8 nm; greater than 5 nm; or greater than 3 nm. ("Bandwidth" can refer to full width half maximum (FWHM) bandwidth). If the MOPA is used as a pump for a FWM process, it is possible that the FWM signal and idler signals can also have a bandwidth larger than preferable for certain CARS imaging processes, due at least in part to the pump bandwidth being undesirably increased during amplification. As an aside, it should be noted that the spectral broadening, such as spectral broadening due to SPM, can occur during processes other than amplification, and, for example, can occur in a passive media (e.g., a passive fibre) as well, depending on, for example, signal (e.g., pulse) power or energy and propagation length.

However, in one aspect of the invention a source 3420 that includes a MOPA or other pump source providing a signal bandwidth larger than desired can be adapted and constructed to provide a more desirable bandwidth for one or more of the signals delivered to the CARS process. For example, the FWM process can be seeded with a signal having bandwidth selected to cause one or more of the FWM signals (pump, idler or FWM signal) to have a bandwidth that is narrower than if the FWM process was not seeded, thus making the FWM signals more useful as the CARS pump or CARS Stokes signal. For example, the seed signal can have a bandwidth selected to be no greater than 1 nm; no greater than 1.5 nm; no greater than 2 nm; no greater than 3 nm, or no greater than 4 nm. Accordingly, one or more of the CARS signals provided to the sample for CARS imaging can have for example, a bandwidth of no greater than 5 nm, or no greater than 3 nm, or no greater than 2 nm, or no greater than 1 nm, where the bandwidth of the signal would be greater absent the seeding. All combinations of the foregoing bandwidths for the seeds and FWM signals are contemplated, as the effect of the bandwidth of the seed on the FWM signals can depend on many factors.

Those skilled in the art will recognize or be able to ascertain using no more than routine experimentation many equivalents to the specific embodiments of the invention described herein. It is therefore to be understood that the foregoing embodiments are presented by way of example only and that within the scope of the appended claims and equivalents thereto, the invention may be practiced otherwise than as specifically described. The present disclosure is directed to each individual feature, system, material and/or method described herein. In addition, any combination of two or more such features, systems, materials and/or methods, if such features, systems, materials and/or methods are not mutually inconsistent, is included within the scope of the present invention.

In the claims as well as in the specification above all transitional phrases such as "comprising," "including," "carrying," "having," "containing," "involving" and the like are understood to be open-ended.

The phrase "A or B" as in "one of A or B" is generally meant to express the inclusive "or" function, meaning that all three of the possibilities of A, B or both A and B are included, unless the context clearly indicates that the exclusive "or" is appropriate (i.e., A and B are mutually exclusive and cannot be present at the same time).

It is generally well accepted that "a" means "at least one" or "one or more. For clarity, as used herein "a" and the like mean "at least one" or "one or more." The phrase "at least one" may at times be explicitly used to emphasize this point. Use of the phrase "at least one" in one claim recitation is not to be taken to mean that the absence of such a term in another recitation (e.g., simply using "a") is somehow more limiting. Furthermore, later reference to the term "at least one" as in "said at least one" should not be taken to introduce additional limitations absent express recitation of such limitations. For example, recitation that an apparatus includes "at least one widget" and subsequent recitation that "said at least one widget is coloured red" does not mean that the claim requires all widgets of an apparatus that has more than one widget to be red. The claim shall read on an apparatus having one or more widgets provided simply that at least one of the widgets is coloured red.

The invention claimed is:

1. An optical source comprising:
    an optical output arranged to output an output optical signal;
    a pump optical source arranged to generate an optical signal at a pump wavelength;
    an optical splitter arranged to receive the optical signal and to split the optical signal into a pump signal and a seed pump signal;
    a seed signal forming apparatus arranged to receive the seed pump signal at the pump wavelength and to transform the seed pump signal into a seed signal at a seed wavelength; and
    a first microstructured optical fibre arranged to receive the pump signal and the seed signal, the first microstructured optical fibre being arranged to cause the pump signal to undergo four-wave mixing seeded by the seed signal on transmission through the first microstructured optical fibre such that a first optical signal at a signal wavelength and second optical signal at an idler wavelength are generated, one of the signal wavelength and the idler wavelength being the seed wavelength and one of the first and second optical signals being provided to the optical output to form the output optical signal.

2. An optical source as claimed in claim 1, wherein the seed signal forming apparatus comprises:
    a first optical fibre arranged to cause the seed pump signal to undergo spectral broadening on transmission through the first optical fibre to thereby form an optical supercontinuum signal; and
    a first optical filter having a filter bandwidth and being arranged to receive the optical supercontinuum signal and to select a part of the optical supercontinuum signal within the filter bandwidth.

3. An optical source as claimed in claim 1, wherein the seed signal forming apparatus comprises:
    a further microstructured optical fibre arranged to cause the seed pump signal to undergo four-wave mixing on transmission there through such that a first signal seed at the signal wavelength and a first idler seed at the idler wavelength are thereby generated; and
    a second optical filter arranged to select said one of the first signal seed and the first idler seed to form the seed signal.

4. An optical source as claimed in claim 1, wherein the optical source further comprises:
    a second microstructured optical fibre arranged to receive a second pump signal comprising one of the first and second optical signals from the first microstructured optical fibre and to cause the second pump signal to undergo four-wave mixing on transmission through the second microstructured optical fibre such that a third optical signal at a second signal wavelength and a fourth optical signal at a second idler wavelength are generated, one of the third and fourth optical signals being provided to the optical output instead of or in addition to said one of said first and second optical signals.

5. An optical source as claimed in claim 2, wherein the optical source further comprises:
    a second microstructured optical fibre arranged to receive a second pump signal comprising one of the first and second optical signals from the first microstructured optical fibre and to cause the second pump signal to undergo four-wave mixing on transmission through the second microstructured optical fibre such that a third optical signal at a second signal wavelength and a fourth optical signal at a second idler wavelength are generated, one of the third and fourth optical signals being provided to the optical output instead of or in addition to said one of said first and second optical signals.

6. An optical source as claimed in claim 3, wherein the optical source further comprises:
    a second microstructured optical fibre arranged to receive a second pump signal comprising one of the first and second optical signals from the first microstructured optical fibre and to cause the second pump signal to undergo four-wave mixing on transmission through the second microstructured optical fibre such that a third optical signal at a second signal wavelength and a fourth optical signal at a second idler wavelength are generated, one of the third and fourth optical signals being provided to the optical output instead of or in addition to said one of said first and second optical signals.

7. An optical source as claimed in claim 4, wherein the seed signal forming apparatus comprises:
    a first optical fibre arranged to cause the seed pump signal to undergo spectral broadening on transmission through the first optical fibre to thereby form an optical supercontinuum signal and a first optical filter having a filter bandwidth and being arranged to receive the optical supercontinuum signal and to select a part of the optical supercontinuum signal within the filter bandwidth;
    wherein the first optical filter comprises a wavelength dependent optical splitter arranged to split the optical supercontinuum signal into a first part comprising the seed signal and a second part comprising a transmitted optical supercontinuum signal; and wherein the seed signal forming apparatus further comprises a third optical filter having a second filter bandwidth and being arranged to receive the transmitted optical supercontinuum signal and to select a part of the transmitted optical supercontinuum signal within the second filter bandwidth to form a second seed signal at a second seed wavelength, the seed signal forming apparatus further being arranged to deliver the second seed signal to the second microstructured optical fibre such that the second pump signal undergoes four-wave mixing seeded by the second seed signal, such that one of the second signal wavelength and the second idler wavelength comprises the second seed wavelength.

8. An optical source as claimed in claim 4, wherein the seed signal forming apparatus comprises a further microstructured optical fibre arranged to cause the seed pump signal to undergo four-wave mixing on transmission there through such that a first signal seed at the signal wavelength and a first idler seed at the idler wavelength are thereby generated, a second optical filter arranged to select said one of the first signal seed and the first idler seed to form the seed signal;

wherein the seed signal forming apparatus further comprises an optical splitter arranged to receive the seed signal and to split it into a first part to be provided to the first microstructured optical fibre and a second part to form a second seed pump signal; and wherein the optical pulse source further comprises second seed signal forming apparatus arranged to receive the second seed pump signal and to transform the second seed pump signal into a second seed signal at a second seed wavelength, the second seed signal forming apparatus being arranged to deliver the second seed signal to the second microstructured optical fibre such that the second pump pulse undergoes four-wave mixing seeded by the second seed signal, such that one of the second signal wavelength and the second idler wavelength comprises the second seed wavelength.

9. An optical source as claimed in claim 8, wherein the second seed signal forming apparatus comprises:
a second further microstructured optical fibre arranged to cause the second seed pump signal to undergo four-wave mixing on transmission therethrough such that a second signal seed at the second signal wavelength and a second idler seed at the second idler wavelength are thereby generated; and
a fourth optical filter arranged to select one of the second signal seed and the second idler seed to form the second seed signal.

10. An optical source as claimed in claim 4, wherein the optical source further comprises:
a non-linear optical element arranged to receive one of the third and fourth optical signals and to transform the received signal into an output signal comprising a further wavelength, the output signal at the further wavelength being provided to the optical output instead of or in addition to the said one of the first and second optical signals and instead of or in addition to the said one of the third and fourth optical signal.

11. An optical source as claimed in claim 4, wherein the optical signal comprises an optical pulse and the optical source is arranged such that the first microstructured optical fibre receives a resulting pump pulse and a resulting seed pulse at substantially the same time and the second microstructured optical fibre is arranged to receive a resulting second pump pulse and a resulting second seed pulse at substantially the same time.

12. An optical source as claimed in claim 11, wherein the pump optical source is arranged to generate a plurality of optical pulses and is further arranged to vary at least one of the pulse duration and frequency of the optical pulses.

13. An optical source as claimed in claim 1, wherein at least two of the first optical signal, the second optical signal and the pump optical signal are provided to the optical output to form a plurality of output optical signals at different wavelengths.

14. An optical source as claimed in claim 13, wherein three of said optical signals are provided to the optical output to form three output optical signals at different wavelengths.

15. A tunable frequency conversion arrangement comprising:
an optical source as claimed in claim 13; and
a tunable nonlinear optical element arranged to receive at least two of the output optical signals of the optical source, wherein the nonlinear optical element can be tuned to select one of a plurality of frequency conversion modes, wherein in each said frequency conversion mode one or more of said received signals are caused to undergo a nonlinear process on transmission through the nonlinear element such that a frequency-converted optical signal is generated.

16. A tunable frequency conversion arrangement comprising:
an optical source as claimed in claim 14; and
a tunable nonlinear optical element arranged to receive at least two of the output optical signals of the optical source, wherein the nonlinear optical element can be tuned to select one of a plurality of frequency conversion modes, wherein in each said frequency conversion mode one or more of said received signals are caused to undergo a nonlinear process on transmission through the nonlinear element such that a frequency-converted optical signal is generated.

17. A tunable frequency conversion arrangement as claimed in claim 15, wherein the nonlinear process comprises sum frequency generation or difference frequency generation.

18. A tunable frequency conversion arrangement as claimed in claim 17, wherein the nonlinear process comprises difference frequency generation.

19. A tunable frequency conversion arrangement as claimed in claim 17, wherein the nonlinear process comprises sum frequency generation.

20. A tunable frequency conversion arrangement as claimed in claim 16, wherein the nonlinear process comprises sum frequency generation or difference frequency generation.

* * * * *